United States Patent [19]

Sanchez

[11] Patent Number: 5,360,867

[45] Date of Patent: Nov. 1, 1994

[54] PROCESS FOR PREPARING BLOCK OR GRAFT COPOLYMERS USING AMINO OR HYDRAZINO PEROXIDES

[75] Inventor: Jose Sanchez, Grand Island, N.Y.

[73] Assignee: ELF Atochem North America, Inc., Philadelphia, Pa.

[21] Appl. No.: 169,808

[22] Filed: Dec. 17, 1993

Related U.S. Application Data

[62] Division of Ser. No. 565,822, Aug. 10, 1990, Pat. No. 5,272,219, which is a division of Ser. No. 233,643, Aug. 18, 1988, Pat. No. 4,956,416.

[51] Int. Cl.$^5$ ............... C08L 51/00; C08L 53/00; C08F 2/00
[52] U.S. Cl. ........................ 525/70; 525/72; 525/73; 525/76; 525/77; 525/78; 525/91; 525/93; 525/94; 525/387; 526/220; 526/227
[58] Field of Search ............. 525/72, 73, 76, 77, 525/78, 91, 93, 94, 327.6, 387; 526/217, 220, 227

[56] References Cited

U.S. PATENT DOCUMENTS

| | | | |
|---|---|---|---|
| 2,769,804 | 11/1956 | Hanson | 525/65 |
| 2,971,939 | 2/1961 | Baer | 525/285 |
| 2,989,517 | 5/1961 | Hanson et al. | 526/60 |
| 3,113,986 | 12/1963 | Breslow et al. | 585/266 |
| 3,236,872 | 2/1966 | Mandy et al. | 560/302 |
| 3,336,267 | 8/1967 | Zimmerman et al. | 526/208 |
| 3,483,276 | 12/1969 | Mahlman | 525/240 |

(List continued on next page.)

FOREIGN PATENT DOCUMENTS

| | | |
|---|---|---|
| 1180497 | 1/1985 | Canada . |
| 1194477 | 10/1985 | Canada . |
| 0056699 | 7/1982 | European Pat. Off. . |
| 0076691 | 4/1983 | European Pat. Off. . |
| 0103148 | 3/1984 | European Pat. Off. . |
| 0233476 | 8/1987 | European Pat. Off. . |
| 0260134 | 3/1988 | European Pat. Off. . |
| 59-221314 | 12/1984 | Japan . |
| 59-221315 | 12/1984 | Japan . |
| 1117515 | 6/1968 | United Kingdom . |
| 1307409 | 2/1973 | United Kingdom . |
| 2102413 | 2/1983 | United Kingdom . |

OTHER PUBLICATIONS

G. DeVito et al., "Functionalization of an Amorphous Ethylene–Propylene Copolymer by Free Radical Initiated Grafting of Unsaturated Molecules," *Journal of Polymer Science: Polymer Chem. Ed.*, vol. 22, pp. 1335–1347 (1984).

E. G. E. Hawkins, "2-Peroxyamines," *Angewandte Chemie*, vol. 12, No. 10, pp. 783–868, (1973) (International Edition in English).

C. Ruchardt et al., *Chem. Ber.* 101, 3957–3962 (1968).

*Primary Examiner*—Paul R. Michl
*Assistant Examiner*—Tae H. Yoon
*Attorney, Agent, or Firm*—Stanley A. Marcus; Royal E. Bright

[57] ABSTRACT

This invention relates to novel reactive amino or hydrazino peroxides (hereinafter generally referred to as "AHP's") and derivatives all having a Structure A:

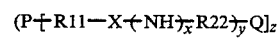

in which the definitions of P, R11, R22, X, Q and x, y and z are given in the Summary Of The Invention section, for example, 4,4-di-(t-butylperoxy)pentanohydrazide (I-1), and the use of these novel compounds in curing unsaturated polyester resins, in initiating polymerization of ethylenically unsaturated monomers, for modifying rheology, for crosslinking and curing olefin polymers and elastomers, for producing novel graft and block copolymers, and for producing novel polymers with covalently bound performance additive functions.

3 Claims, No Drawings

U.S. PATENT DOCUMENTS

| | | | |
|---|---|---|---|
| 3,488,311 | 1/1970 | Burdick et al. | 524/517 |
| 3,509,110 | 4/1970 | DiGiulo et al. | 526/272 |
| 3,553,177 | 1/1971 | Hazen et al. | 526/208 |
| 3,560,455 | 2/1971 | Hazen et al. | 526/272 |
| 3,560,456 | 2/1971 | Hazen et al. | 526/272 |
| 3,560,457 | 2/1971 | Hazen et al. | 526/272 |
| 3,592,948 | 7/1971 | Bafford et al. | 526/220 |
| 3,660,468 | 5/1972 | McKellin | 560/302 |
| 3,671,651 | 6/1972 | D'Angelo | 558/263 |
| 3,706,818 | 12/1972 | Mageli et al. | 525/273 |
| 3,723,375 | 3/1973 | Field et al. | 524/549 |
| 3,884,882 | 5/1975 | Caywood, Jr. | 525/205 |
| 3,919,354 | 11/1975 | Moore et al. | 525/257 |
| 3,952,041 | 4/1976 | D'Angelo et al. | 560/302 |
| 3,991,085 | 11/1976 | Abma et al. | 549/555 |
| 3,998,907 | 12/1976 | DiGiulio | 525/192 |
| 4,072,810 | 2/1978 | D'Angelo et al. | 526/230 |
| 4,097,551 | 6/1978 | DiGiulio et al. | 525/71 |
| 4,108,943 | 8/1978 | Lee et al. | 524/371 |
| 4,129,586 | 12/1978 | Sheppard et al. | 558/387 |
| 4,177,204 | 12/1979 | Mageli et al. | 560/115 |
| 4,180,518 | 12/1979 | Mageli et al. | 558/263 |
| 4,226,952 | 10/1980 | Halasa et al. | 525/192 |
| 4,341,695 | 7/1982 | Lee et al. | 524/342 |
| 4,358,573 | 11/1982 | Verbrugge | 526/272 |
| 4,381,373 | 4/1983 | Ikuma | 525/194 |
| 4,486,570 | 12/1984 | Lordi et al. | 525/93 |
| 4,506,056 | 3/1985 | Gaylord | 524/445 |
| 4,522,983 | 6/1985 | Le-Khac et al. | 525/285 |
| 4,522,992 | 6/1985 | Verbrugge | 526/272 |
| 4,525,308 | 6/1985 | Sanchez | 560/302 |
| 4,665,131 | 5/1987 | Moriya et al. | 525/93 |
| 4,785,063 | 11/1988 | Slongo et al. | 526/259 |
| 4,956,416 | 9/1990 | Sanchez | 525/327.6 |

PROCESS FOR PREPARING BLOCK OR GRAFT COPOLYMERS USING AMINO OR HYDRAZINO PEROXIDES

CROSS REFERENCE TO RELATED APPLICATIONS

This is a division of U.S. patent application Ser. No. 07/565,822, filed Aug. 10, 1990 now U.S. Pat. No. 5,272,219, which is a division of U.S. patent application Ser. No. 07/233,643, filed Aug. 18, 1988, now U.S. Pat. No. 4,956,416.

BACKGROUND OF THE INVENTION

1. Field of the Invention

This invention relates to novel reactive amino or hydrazino peroxides (hereinafter generally referred to as "AHP's") and derivatives all having a Structure A:

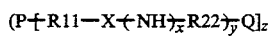  A in which the definitions of P, R11, R22, X, Q and x, y and z are given in the Summary Of The Invention section, for example, 4,4-di-(t-butylperoxy)pentanohydrazide (I-1), and the use of these novel compounds in curing unsaturated polyester resins, in initiating polymerization of ethylenically unsaturated monomers, for modifying rheology, for crosslinking and curing olefin polymers and elastomers, for producing novel graft and block copolymers, and for producing novel polymers with covalently bound performance additive functions.

2. Description of the Prior Art

The novel reactive amino or hydrazino peroxides of the instant invention possess reactive amino or hydrazino functional groups. Peroxides with other types of reactive functional groups are known in the literature and several are sold commercially. Commercially produced peroxides with reactive functional groups include succinic acid peroxide (carboxy group) and oo-t-butyl o-hydrogen monoperoxymaleate (carboxy group). More recently, 3-hydroxy-1,1-dimethylbutyl peroxy-2-ethylhexanoate (hydroxy group) and 3-hydroxy-1,1-dimethylbutyl peroxyneoheptanoate (hydroxy group) have been offered commercially. Such initiators enable polymer producers to enhance the utility and value of polymers by allowing them to 'put' the reactive groups onto polymers by means of free-radical polymerization of ethylenically unsaturated monomers or by means of grafting reactions using these reactive peroxide initiators.

Other reactive initiators are disclosed in the literature. U.S. Pat. No. 3,236,872 discloses hydroxy-peroxides. U.S. Pat. No. 3,991,085 discloses epoxy-peroxides. U.S. Pat. No. 3,660,468 discloses peroxides having reactive carboxy groups, particularly mono-peresters of α,α disubstituted malonic acid. U.S. Pat. No. 3,671,651 discloses peroxides having reactive acylating groups, such as acyl halide groups, haloformate groups or anhydride groups. U.S. Pat. No. 3,952,041 discloses peroxides with reactive acid chloride groups.

The prior art reactive functional peroxides are not as completely or cleanly reactive with co-reactive anhydride containing compounds and polymers as are the reactive amino and hydrazino peroxides of Structure A. Unlike hydroxy compounds, amino and hydrazino compounds form very stable reaction products with cyclic anhydrides, i.e., amic acids and imides. In contrast, hydroxy compounds react to form carboxy esters that are unstable at the elevated temperatures at which imides are very stable. It is very well known that the cyclic imide structure is very stable thermally. Indeed, polyimides belong to a class of polymers that exhibit extremely high thermal stability owing to the cyclic imide linkage. Because of this enhanced thermal stability, polyimides are employed in very high temperature applications.

Some peroxides possessing amino groups are known. E. G. E. Hawkins, *Angewandte Chemie*, Vol. 12, pp. 783–793 (1973) discloses α-aminoperoxides where the amino group is attached to the same carbon atom as the peroxide group, but does not include α-peroxyhydrazines or α-peroxyazo compounds. For example, this reference indicates that 1-hydroperoxycyclohexylamine is known but is relatively unstable at room temperature. Reaction of 1-hydroperoxyalkylamines with ketones and aldehydes yield 1,2,4-dioxazolidines which are cyclic peroxyamines. Such 1,2,4-dioxazolidines have only one —NH bond, hence, they cannot be used to synthesize stable peroxyimides. The terminal —NH$_2$ groups of the AHP's of Structure A of the present invention are distanced from the peroxide functional group of the AHP's, hence, the AHP's are considerably more stable and more useful than 1-peroxyalkylamines or the 1,2,4-dioxazolidines.

Diperoxyketals and diperoxyketal salts derived from 2,2,6,6-tetraalkyl-4-piperidinone and 1,2,2,6,6-pentaalkyl-4-piperidinone have been disclosed in Canadian Patent 1,194,477, issued Oct. 1, 1985. However, the amino function of these compounds is quite hindered and is quite non-reactive with cyclic anhydrides.

The derivatives of the AHP's of the instant invention within Structure A are novel. Amino peroxides are disclosed in the previously cited Hawkins article and in U.S. Pat. No. 4,180,518. The Hawkins article discloses N-acyl derivatives of 1-peroxyalkylamines. U.S. Pat. No. 4,180,518 discloses carbamate derivatives of dialkyl peroxides, monoperoxycarbonates and peroxycarbamates.

U.S. Pat. No. 4,072,810 discloses coupled peroxides but does not include the coupled peroxides of the present invention. The coupled peroxides of the present invention, derived from the AHP's, are coupled with either a urea functional group or a carbazate functional group.

U.S. Pat. No. 3,706,818 discloses polyperoxy sequential radical initiators (sequential peroxides), but not the sequential peroxides of the present invention which are derived from the AHP's and within Structure A. The sequential peroxides of the present invention are coupled with a carbazate functional group.

With respect to peroxy UV stabilizers derived from the AHP's, U.S. Pat. No. 4,129,586 discloses (column 22, lines 42 through 55) that the patented free radical initiators containing UV stabilizer groups can be prepared by a variety of techniques including reacting a UV stabilizer containing an acylating functional group with an azo or peroxide containing a reactive —OH, —SH or —NH group, among other techniques.

The peroxy UV stabilizers of the present invention, i.e., those derived from the novel AHP's of this invention, are prepared by reacting a UV stabilizer having an acylating function with a peroxide having a reactive hydrazide group.

With respect to the novel polymeric derivatives of the AHP's of this invention, the inventor of the instant invention is unaware of any published art pertaining to peroxy polymers having peroxy groups covalently bound to the polymer via amic acid or imide moieties.

There is a need in the polymer industry for reactive functionalized initiators (peroxides and azos) which can be used to produce reactive, functionalized polymers or peroxy-polymers by various means such as free-radical polymerization of ethylenically unsaturated monomers, grafting onto polymers, chain termination of condensation polymers, reaction with co-functionalized polymers, etc. When the initiator group of the functionalized initiator decomposes in these processes, polymers with functional groups (i.e., at chain ends or pendant from the chains) are produced. Such polymers can be chain extended to produce desirable high performance polymers. This technique is the basis for the high solids acrylic coatings business in which hydroxy-containing low molecular weight acrylic copolymers are chain extended and/or cross linked with co-reactive compounds after being applied in automotive coatings applications, When a reactive functional initiator is used to chain terminate condensation polymers or to react with co-reactive polymers, polymers with pendant initiator groups and/or initiator end groups are produced. These peroxy-polymers can then be used to produce block or graft copolymers that can be used in compatibilizing polymer blends and alloys produced from incompatible polymers.

Because of this there is a need for reactive functional initiators that are reactive with commercially available and inexpensive co-reactive polymers. The co-reactive polymers that are available include those which have hydroxy groups, such as poly(vinyl alcohol) and acrylic copolymers derived from hydroxyalkyl acrylates and methacrylates; those which have carboxy groups, such as maleic acid, fumaric acid, acrylic acid and methacrylic acid polymers; and anhydride copolymers, such as those derived from maleic anhydride and acrylic acid anhydride.

Reactive functionalized initiators that are co-reactive with hydroxy polymers are those having acid halide, haloformate or anhydride groups. In general, the reaction requires the presence of a base, hence, the reactions have to be done in a solvent rather in more convenient polymer mixing equipment such as an extruder.

Reactions between polymers with carboxy groups and initiators with co-reactive groups are sluggish unless the carboxy groups are initially converted to acid halide groups. The latter reaction has to be done in solution as would the subsequent reaction between the polymer with acid halide groups and the initiator with co-reactive groups (e.g., hydroxy groups). Polymer solution reactions are inconvenient and are expensive to run.

Reactions between polymers with anhydride groups and co-reactive initiators appear to have potential for producing polymeric peroxides economically. Making these polymeric substrates even more attractive is the fact that numerous anhydride copolymers are commercially available as low cost resins. Available are styrene/maleic anhydride (MA) copolymers, ethylene/MA copolymers, octadecene/MA copolymers, alkyl vinyl ether/MA copolymers, grafted MA modified polyolefins and others. However, the reaction between a hydroxy containing peroxide and a MA copolymer is expected to give a poly(carboxy ester) with pendant peroxide functions. At elevated temperatures the peroxy polymer is expected to decompose to yield the MA copolymer and the hydroxy containing peroxide. In comparison, the AHP's of the instant invention react with MA copolymers to initially form poly(peroxy amic acid) polymers which on heating to elevated temperatures further react, with elimination of water, to give poly(peroxyimide) polymers with thermally stable imide groups.

SUMMARY OF THE INVENTION

The present invention concerns a peroxide compound having reactive amino or hydrazino functional groups capable of forming a stable amic acid or cyclic imide compound in a reaction with a cyclic anhydride, where there are at least 2 carbon atoms between the reactive amino or hydrazino functional group and the peroxide group. As used herein, "peroxide group" means the —OO— group.

The present invention also relates to amino or hydrazino peroxides (AHP's) and derivatives of Structure A:

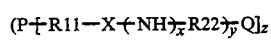

where x is 0 or 1, y is 1 or 2 and z is 1 to 3, with the further provisos that when y is 2, z can only be 1 and when z is 2 or 3, y can only be 1, and (I) when y is 1 and z is 1, P is a peroxide-containing mono-radical having a structure:

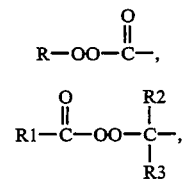

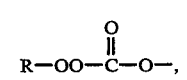

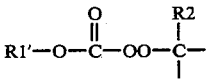

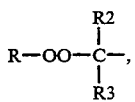

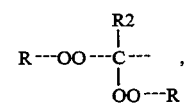

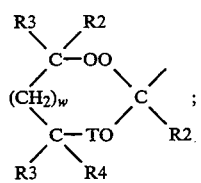

where
w is 1 or 2;
R is a substituted or unsubstituted t-alkyl radical of 4 to 12 carbons, a substituted or unsubstituted t-aralkyl radical of 9 to 13 carbons, a t-cycloalkyl radical of 5 to 12 carbons or a substituted or unsubstituted t-alkynyl radical of 5 to 10 carbons;

R1 is a substituted or unsubstituted, branched or unbranched, alkyl radical of 1 to 13 carbons, a substituted or unsubstituted cycloalkyl radical of 5 to 10 carbons, a substituted or unsubstituted, branched or unbranched, aralkyl radical of 7 to 11 carbons, or a substituted or unsubstituted aryl radical of 6 to 10 carbons;

R1' is a substituted or unsubstituted, branched or unbranched, alkyl radical of 1 to 13 carbons, a substituted or unsubstituted cycloalkyl radical of 5 to 10 carbons, or a substituted or unsubstituted, branched or unbranched, aralkyl radical of 7 to 11 carbons;

R2 and R3 are the same or different and are substituted or unsubstituted alkyl radicals of 1 to 4 carbons;

the substituents for R, R1, R1', R2 and R3 being alkyl radicals of 1 to 4 carbons, chloro or bromo;

R4 is hydrogen, a substituted or unsubstituted alkyl radical of 1 to 10 carbons or a substituted or unsubstituted aryl radical of 6 to 10 carbons, the R4 substituents being one or more alkyl radicals of 1 to 8 carbons, chloro, bromo or carboxy;

T is nothing or —O—;

R11 is a substituted or unsubstituted alkylene diradical of 2 to 8 carbons or a substituted or unsubstituted 1,2-, 1,3- or 1,4-phenylene diradical, the R11 substituents being alkyl radicals of 1 to 4 carbons, chloro or bromo;

X is nothing,

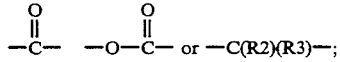

R22 is nothing, a substituted or unsubstituted alkylene diradical of 2 to 10 carbons or a substituted or unsubstituted 1,2-, 1,3- or 1,4-phenylene diradical, the R22 substituents being alkyl radicals of 1 to 3 carbons, chloro or bromo;

Q is a nitrogen-containing radical having a nitrogen-containing structure (a), (b), (c), (d) or (e), or a recurring unit in a polymer having a structure (f) or (g):

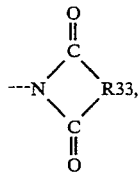 (a)

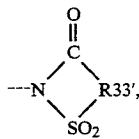 (b)

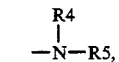 (c)

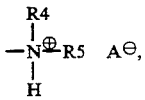 (d)

—N=R8, (e)

where

R33 is a substituted or unsubstituted 1,2- or 1,3- alkylene diradical of 2 to 18 carbons, a substituted or unsubstituted 1,2- or 1,3-alkenylene diradical of 2 to 18 carbons, a substituted or unsubstituted 1,2-cycloalkylene diradical of 5 to 6 carbons, a substituted or unsubstituted 1,2-cycloalkenylene diradical of 5 to 6 carbons, a substituted or unsubstituted 1,2-bicycloalkylene diradical of 7 to 9 carbons, a substituted or unsubstituted 1,2-bicycloalkenylene diradical of 7 to 9 carbons, a substituted or unsubstituted 1,2-phenylene diradical, a substituted or unsubstituted 1,2-naphthenylene diradical, a substituted or unsubstituted 2,3-naphthenylene diradical or a substituted or unsubstituted 1,8-naphthenylene diradical, the R33 substituents being one or more alkyl radicals of 1 to 8 carbons, chloro, bromo, nitro, carboxy, alkoxy radicals of 1 to 8 carbons or alkoxycarbonyl radicals of 2 to 9 carbons;

R33' is a substituted or unsubstituted 1,2-phenylene diradical, the R33' substituents being one or more alkyl radicals of 1 to 8 carbons, chloro or bromo;

A- is chloride, bromide, sulfate, acid sulfate, phosphate, acid phosphate, p-methylphenylsulfonate, phenylsulfonate, methylsulfonate, phenylphosphonate, cyclohexylphosphonate or carboxylate from any carboxylic acid;

R5 is hydrogen, a substituted or unsubstituted acyl radical of 1 to 18 carbons, a substituted or unsubstituted alkenoyl radical of 3 to 10 carbons, a perfluoroacyl radical of 2 to 18 carbons, a substituted or unsubstituted aroyl radical of 7 to 11 carbons, a substituted or unsubstituted cycloalkylcarbonyl radical of 6 to 13 carbons, a substituted or unsubstituted cycloalkenylcarbonyl radical of 6 to 13 carbons, a substituted or unsubstituted bicycloalkylcarbonyl radical of 6 to 13 carbons, a substituted or unsubstituted alkoxycarbonyl radical of 2 to 19 carbons, a substituted or unsubstituted alkenyloxycarbonyl radical of 3 to 8 carbons, a substituted or unsubstituted aryloxycarbonyl radical of 7 to 11 carbons, a substituted or unsubstituted cycloalkoxycarbonyl radical of 6 to 13 carbons, a substituted or unsubstituted alkylaminocarbonyl radical of 2 to 19 carbons, a substituted or unsubstituted alkenylaminocarbonyl radical of 3 to 8 carbons, a substituted or unsubstituted arylaminocarbonyl radical of 7 to 11 carbons, an alkylsulfonyl radical of 1 to 8 carbons, a substituted or unsubstituted arylsulfonyl radical of 6 to 10 carbons, or a radical having a structure (h), (i), (j), (k) or (l):

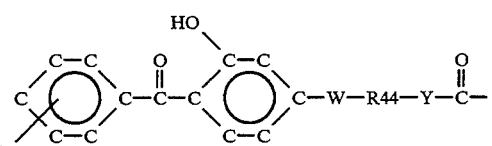 (h)

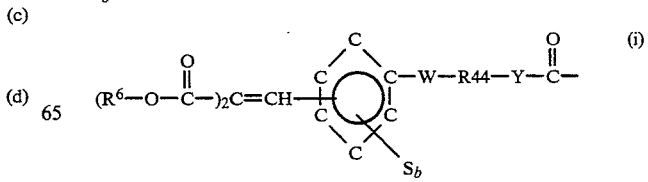 (i)

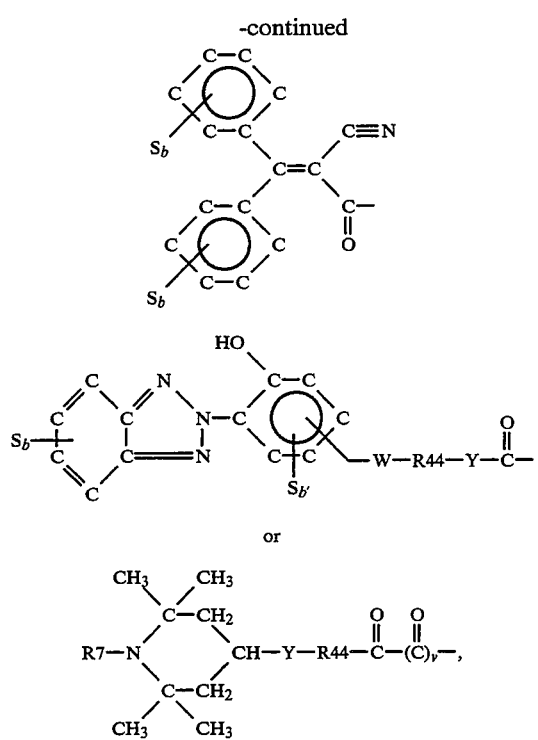

(j)

(k)

(l)

where
W is nothing,

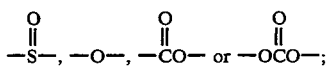

Y is —NH—, —S—, —SO—, —SO$_2$ or —O—;

R6 is an alkyl radical of 1 to 18 carbons, an aryl radical of 6 to 12 carbons or an aralkyl radical of 7 to 11 carbons;

R7 is H, an alkyl radical of 1 to 4 carbons, an acyl radical of 2 to 18 carbons, an aroyl radical of 7 to 15 carbons, an alkoxycarbonyl radical of 2 to 19 carbons or an aryloxycarbonyl radical of 7 to 15 carbons;

R44 is nothing or an alkylene diradical of 1 to 6 carbons, and preferably, 1 to 3 carbons;

v is 0 or 1;

S$_b$ is nothing or one or more of alkyl radicals of 1 to 4 carbons, lower alkoxy, chloro, bromo, cyano or nitro;

S$_b$' is nothing or one or more of alkyl radicals of 1 to 4 carbons, t-butyl radicals, t-amyl radicals, t-octyl radicals, alpha-cumyl radicals, alkoxy radicals of 1 to 4 carbons, chloro, bromo, cyano or nitro;

the R5 substituents being one or more alkyl radicals of 1 to 8 carbons, chloro, bromo, nitro, carboxyl, alkoxy radicals of 1 to 8 carbons or alkoxycarbonyl radicals of 2 to 9 carbons, with the proviso that when R22 is nothing, the R5 substituents can additionally be a t-alkylperoxycarbonyl radical of 5 to 9 carbons, a t-alkylperoxycarbonyloxy radical of 5 to 9 carbons, or a t-alkylperoxy radical of 4 to 8 carbons;

R8 is a substituted or unsubstituted alkylidene diradical of 2 to 12 carbons, a substituted or unsubstituted cycloalkylidene diradical of 5 to 12 carbons, optionally possessing as one or more heteroatoms N, O or S in the cycloalkylidene chain, or a substituted or unsubstituted benzylidene diradical of 7 to 11 carbons, the R8 substituents being one or more alkyl radicals of 1 to 8 carbons, chloro, bromo, carboxy or nitro;

the recurring unit in polymer structures (f) and (g) being, respectively:

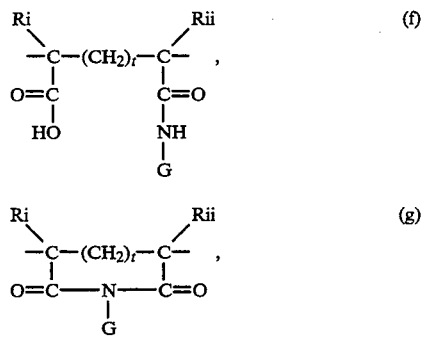

in which the recurring units (f) or (g) occur in the polymer backbone or as pendant units or both, where Ri and Rii are the same or different and are hydrogen, an alkyl radical of 1 to 6 carbons, a cycloalkyl radical of 5 to 7 carbons, phenyl, chloro or bromo;

t is 0 or 1; and

G shows the point of attachment of group Q to the residue of Structure A;

(II) when y is 1 and z is 2,

P is a peroxide-containing diradical having a structure:

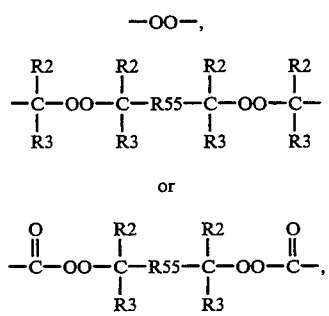

where

R55 is an alkylene diradical of 1 to 6 carbons, an alkynylene diradical of 2 to 6 carbons, an alkadiynylene diradical of 4 to 8 carbons or a 1,3- or 1,4-phenylene diradical; and R11, X, R22, Q, R, R1, R2, R3 and x are the same as when y is 1 and z is 1, with the proviso that Q cannot be the above-defined recurring unit (f) or (g) in a polymer;

(III) when y is 1 and z is 3,

P is a peroxide-containing tri-radical having a structure:

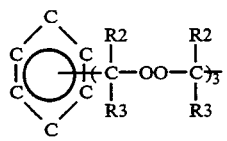

where

R11, X, R22, Q, R, R1, R2, R3 and x are the same as when y is 1 and z is 1, with the proviso that Q cannot be the above-defined recurring unit in a polymer; and (IV) when z is 1 and y is 2, P, R11 and X are the same as when y is 1 and z is 1;

R22 is nothing; and

Q is a nitrogen-containing diradical having a structure (m), (n) or (o):

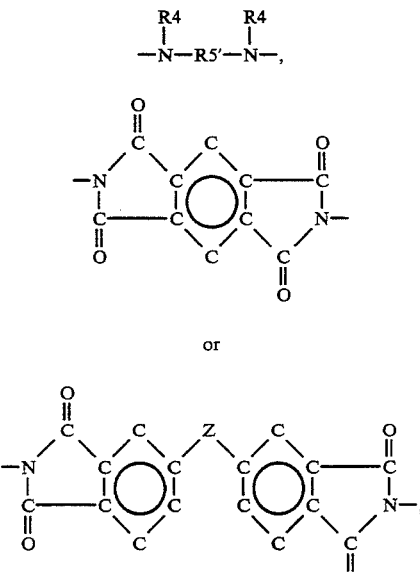

where

R5' is —SO$_2$—,

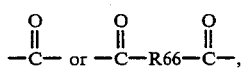

where R66 is nothing or a diradical having a structure:

—R77—,
—Y—R77—Y—,
—R77—Z—R77— or
—Y—R77—Z—R77—Y—, where

R77 is a substituted or unsubstituted alkylene diradical of 2 to 10 carbons, optionally having one or more —O— or —S— heteroatoms in the alkylene chain, or a substituted or unsubstituted 1,2-, 1,3- or 1,4-phenylene diradical, the R77 substituents being one or more alkyl radicals of 1 to 8 carbons, chloro, bromo, carboxy, nitro or alkoxy radicals of 1 to 8 carbons;

Z is nothing or a substituted or unsubstituted alkylene diradical of 1 to 8 carbons, or a diradical having a structure:

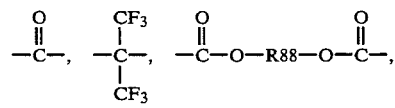

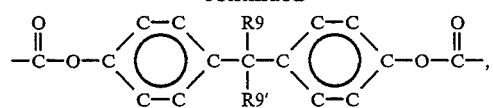

where

R9 and R9' are the same or different and are hydrogen or alkyl radicals of 1 to 10 carbons, and R9 and R9' can be connected together to form a carbocyclic ring containing 5 to 12 carbons and having substituents of one or more alkyl radicals of 1 to 4 carbons; and R88 is a substituted or unsubstituted alkylene diradical of 2 to 10 carbons, the R88 substituents being alkyl of 1 to 8 carbons, chloro, bromo, carboxy, alkoxy radicals of 1 to 8 carbons, alkoxycarbonyl radicals of 1 to 8 carbons, acyloxycarbonyl radicals of 1 to 8 carbons or nitro.

Other aspects of the present invention include:

A. Novel processes for curing an unsaturated polyester resin by reacting the resin in the presence of an amount of an AHP of Structure A under conditions effective to cure the resin.

B. Novel processes for preparing novel polymeric peroxides of Structure A, where Q is a recurring unit having a structure

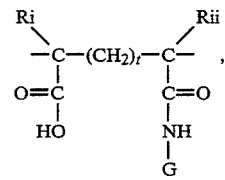

or

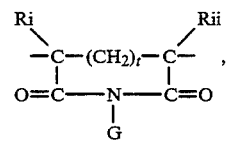

in which the units occur in the polymer backbone or as pendant units or both, and where G shows the point of attachment of group Q to the residue of Structure A, by reacting an anhydride-containing copolymer with recurring units of the structure

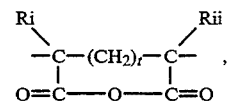

in which the units occur in the polymer backbone or as pendant units or both, with novel non-polymeric AHP's of Structure A, where Q is —NH$_2$, where the reaction occurs in solution or in a polymer melt under conditions effective for preparing the novel polymeric peroxides.

C. Novel processes for initiating the polymerization of ethylenically unsaturated monomers by reacting the monomers with an initiating amount of an AHP of Structure A and under conditions effective to initiate polymerization of the monomers. Typical monomers include, for example, styrene, ethylene and vinyl chloride.

D. Novel processes for curing elastomeric resins by reacting the resins in the presence of an initiating amount of an AHP of Structure A and under conditions effective to cure the elastomeric resins. Typical elastomeric resins include, for example, ethylene-propylene copolymers (EPR), ethylene-propylene-diene terpolymers (EPDM), and butadiene rubbers.

E. Novel processes for modifying polymers by varying the molecular weight and modifying the molecular weight distribution of the polymers, namely, polypropylene (PP), or copolymers comprising more than 50% by weight of polypropylene, by reacting the polymer or copolymer in the presence of an amount of an AHP of Structure A and under conditions effective to modify the polymer or copolymer.

F. Novel processes for crosslinking olefin polymers by reacting the polymers in the presence of an amount of an AHP of Structure A and under conditions effective to crosslink the polymers. Typical olefin polymers include, for example, low density polyethylene (LDPE), linear low density polyethylene (LLDPE) and high density polyethylene (HDPE)

G. Novel processes for preparing polymers with covalently bound performance additive functional groups by reacting with the polymers an AHP of Structure A having at least one performance additive functional group under conditions effective to covalently bond the AHP to the polymers in a manner to enhance the performance of the polymers. Preferably, the performance additive functional groups are groups (h), (i), (j), (k) or (l) of Structure A as set forth above.

H. Novel processes for preparing novel block or graft polymers useful for compatibilizing blends and alloys of two or more polymers by reacting with the polymers or monomers used to form the block or graft copolymers a polymeric peroxide of Structure A under conditions effective to form the block or graft copolymers.

The amounts of reactants and the reaction conditions of the above summarized processes, such as temperature, time, pressure, addition rates, etc., would be well known to those skilled in the art based on the disclosure herein, or would be readily discernible therefrom without undo experimentation.

DETAILED DESCRIPTION OF THE PREFERRED EMBODIMENTS

Preparation of the Novel Amino or Hydrazino Peroxides (AHP's) of Structure A

Several synthesis processes are available for preparing the novel AHP's possessing terminal amino groups.

One process is to react excess hydrazine or diamine with a peroxide possessing an acid halide functional group, a haloformate functional group, an acid anhydride functional group or an ester functional group. In the cases where excess hydrazine or a diamine is reacted with a peroxide possessing an acid halide functional group, a haloformate functional group or an acid anhydride functional group, the excess hydrazine or diamine acts as the base in the reaction. Alternately, another base can be used with the hydrazine or diamine, such as triethylamine, tributylamine, N,N-dimethylaniline, sodium hydroxide, sodium carbonate, sodium hydrogen carbonate, potassium hydroxide, potassium carbonate, potassium hydrogen carbonate, calcium hydroxide, barium hydroxide, calcium carbonate and trisodium phosphate, for example.

Useful forms of hydrazine in these processes include anhydrous hydrazine as well as aqueous hydrazine compositions, e.g., 85% hydrazine hydrate (54.4% hydrazine). Useful diamines in these processes include ethylenediamine, 1,4-butylenediamine, hexamethylenediamine, 1,4-phenylenediamine, 1,3-phenylenediamine and others.

Useful peroxides possessing acid halide functional groups, haloformate functional groups, acid anhydride functional groups and ester functional groups can be prepared by methods well known in the art and include, for example, 2-(t-butylperoxycarbonyl)benzoyl chloride, 3-(t-butylperoxycarbonyl)propionyl chloride, 4-(t-amylperoxycarbonyl)butyryl chloride, 4,4-di-(t-butylperoxy)pentyl chloroformate, 1,3-dimethyl-3-(t-butylperoxy)butyl chloroformate, 3-methyl-3-(t-butylperoxy)butyl chloroformate, 1,3-dimethyl-3-(t-amylperoxy)butyl chloroformate, 1,3-dimethyl-3-(2-ethylhexanoylperoxy)butyl chloroformate, 1,3-dimethyl-3-(neoheptanoylperoxy)butyl chloroformate, di-(1,1-dimethyl-3-chlorocarbonyloxybutyl) peroxide, di-(1,1-dimethyl-3-chlorocarbonyloxypropyl) peroxide, 4,4-di-(t-butylperoxy)pentanoic acid anhydride, methyl 3,3-di-(t-butylperoxy)butyrate, methyl 3,3-di-(t-amylperoxy)butyrate, n-butyl 3,3-di-(t-butylperoxy)butyrate, phenyl 3,3-di-(t-butylperoxy)butyrate, methyl 4,4-di-(t-butylperoxy)pentanoate, ethyl 4,4-di-(t-butylperoxy)pentanoate, n-butyl 4,4-di-(t-butylperoxy)pentanoate, phenyl 4,4-di-(t-butylperoxy)pentanoate, t-butyl 4,4-di-(t-butylperoxy)pentanoate, 3-(methoxycarbonylmethyl)-3,5,7,7-tetramethyl-1,2,4-trioxacycloheptane, 3-(2-ethoxycarbonylethyl)-3,5,7,7-tetramethyl-1,2,4-trioxacycloheptane, 3-(methoxycarbonylmethyl)-3,6,6,9,9-pentamethyl-1,2,4,5-tetraoxacyclononane and 3-(2-ethoxycarbonylethyl)-3,6,6,9,9-pentamethyl-1,2,4,5-tetraoxacyclononane.

Another synthesis route to AHP's possessing terminal amino groups involves using 1-(1-isocyanato-1-methylethyl)-4-isopropenylbenzene as the starting material. Initially the latter reactant is reacted with an alcohol, for example, methanol, to form O-methyl N-(1-methyl-1-[4-isopropenylphenyl]ethyl) carbamate. Subsequently, this intermediate is reacted with a hydroperoxide, for example, t-butyl hydroperoxide, in the presence of an acid catalyst, such as anhydrous hydrogen chloride, sulfuric acid and/or p-toluenesulfonic acid. The resulting product, O-methyl N-(1-methyl-1-[4-(1-methyl-1-[t-butylperoxy]ethyl)phenyl]ethyl) carbamate, is subsequently hydrolyzed in the presence of the above-identified or other suitable, well known acid or base catalyst to yield the amino-peroxide, 1-(1-amino-1-methylethyl)-4-(1-methyl-1-[t-butylperoxy]ethyl)benzene.

Non-limiting examples of the novel AHP's possessing a terminal amino group include the following:

AHP's With Terminal Amino Groups
4,4-Di-(t-butylperoxy)pentanohydrazide
4,4-Di-(t-amylperoxy)pentanohydrazide
3,3-Di-(t-butylperoxy)butanohydrazide
3-(1,4,4,6-Tetramethyl-2,3,7-trioxacycloheptyl)propionhydrazide
N-(2-Aminoethyl) 4,4-di-(t-butylperoxy)pentamide 1,3-Dimethyl-3-(t-butylperoxy)butyl carbazate
1,3-Dimethyl-3-(t-amylperoxy)butyl carbazate
1,3-Dimethyl-3-(2-ethylhexanoylperoxy)butyl carbazate
1,3-Dimethyl-3-(neoheptanoylperoxy)butyl carbazate
1,3-Dimethyl-3-(neodecanoylperoxy)butyl carbazate
4,4-Di-(t-butylperoxy)pentyl carbazate
O-(1,3-Dimethyl-3-[t-butylperoxy]butyl) N-(2-aminoethyl) carbamate, also known by the alternate name 1,3-dimethyl-3-(t-butylperoxy)butyl N-(2-aminoethyl) carbamate
O-(1,3-Dimethyl-3-[t-butylperoxy]butyl) N-(6-aminohexyl) carbamate
O-(1,3-Dimethyl-3-[2-ethylhexanoylperoxy]butyl) N-(2-aminoethyl) carbamate
O-(4,4-Di-[t-butylperoxy]pentyl) N-(2-aminoethyl) carbamate
1-(1-Amino-1-methylethyl)-4-(1-methyl-1-[t-butylperoxy]ethyl)benzene
1-(1-Amino-1-methylethyl)-3-(1-methyl-1-[t-butylperoxy]ethyl)benzene Derivatives of AHP's Within Structure A Novel derivatives of the above defined AHP's can be synthesized by reacting the AHP's with compounds that are reactive with the amino functional group of the AHP's. Bases useful in these reactions include the bases listed above. Such reactive compounds include acid halides, chloroformates, carboxylic acid anhydrides, sulfonyl halides, isocyanates, ketones and aldehydes, alkylating agents, epoxides, acrylonitrile, methacrylonitrile and organic or mineral acids.

Reacting AHP's with acid halides, such as acetyl chloride, butyryl chloride, pivaloyl chloride, 2-ethylhexanoyl chloride, neodecanoyl chloride, stearoyl chloride, acryloyl chloride, methacryloyl chloride, dodecanedioyl dichloride, adipoyl chloride, benzoyl chloride, 2-methylbenzoyl chloride, 4-methylbenzoyl chloride, 2(methoxycarbonyl)benzoyl chloride, 2-(2-ethylhexoxycarbonyl)benzoyl chloride, 2-naphthoyl chloride, phthaloyl chloride and terephthaloyl chloride, results in the formation of acyl substituted amide, carbazate or hydrazide derivatives.

Reacting AHP's with chloroformates such as methyl chloroformate, isopropyl chloroformate, 2-ethylhexyl chloroformate, hexadecyl chloroformate, 2-(acryloxyethyl) chloroformate, methacryloxypropyl chloroformate, 2-phenoxyethyl chloroformate, ethylene glycol bischloroformate, diethylene glycol bischloroformate, phenyl chloroformate, bisphenol A bischloroformate, results in the formation of alkoxycarbonyl or aryloxycarbonyl substituted amide, carbazate or hydrazide derivatives.

Reacting AHP's with carboxylic acid anhydrides, such as acetic anhydride, maleic anhydride, itaconic anhydride, succinic anhydride, glutaric anhydride, 1-dodecene-succinic anhydride, phthalic anhydride, trimellitic anhydride, pyromellitic dianhydride and benzophenone dianhydride, results in the formation of acyl or carboxyacyl substituted amide, carbazate or hydrazide derivatives or substituted imide derivatives.

Reacting AHP's with sulfonyl halides, such as p-methylphenylsulfonyl chloride and methylsulfonyl chloride, results in the formation of sulfonyl substituted amide, carbazate or hydrazide derivatives.

Reacting AHP's with isocyanates, such as phenyl isocyanate, methyl isocyanate, hexamethylene diisocyanate, toluene diisocyanate, diphenylmethane diisocyanate and isophorone diisocyanate, results in the formation of alkylaminocarbonyl or arylaminocarbonyl substituted amide, carbazate or hydrazide derivatives.

Reacting AHP's with ketones and aldehydes such as acetone, 2-butanone, 2-hexanone, cyclohexanone, 4-methylcyclohexanone, 4-t-butylcyclohexanone, formaldehyde, acetaldehyde, benzaldehyde, p-methoxybenzaldehyde and furfuraldehyde, results in the formation of Schiff base or hydrazone derivatives.

Reacting AHP's with alkylating agents, such as alkyl and aralkyl halides (bromides and chlorides) and sulfates, alkylsulfonates and arylsulfonates, and epoxides, such as ethylene oxide, propylene oxide and epichlorohydrin, results in the formation of N-alkyl substituted amide, carbazate or hydrazide derivatives.

Reacting AHP's with organic or mineral acids, such as formic acid, acetic acid, chloroacetic acid, trifluoroacetic acid, lauric acid, adipic acid, benzoic acid, phthalic acid, trimellitic acid, methylsulfonic acid, p-methylphenylsulfonic acid, hydrochloric acid, hydrobromic acid, nitric acid, sulfuric acid, phosphoric acid and perchloric acid, results in salt formation.

Non-limiting examples of the derivatives of the novel AHP's include the following:

Derivatives of AHP's
1-Benzoyl-2-(4,4-di-[t-butylperoxy]pentanoyl)hydrazine
1-(2-Ethylhexoxycarbonyl]-2-[4,4-di-[t-butylperoxy]pentanoyl)hydrazine
3-Oxapentane-1,5-diyl bis(2-[4,4-di-(t-butylperoxy)pentanoyl]carbazate)
2,2'-Di-(3,3-di-[t-butylperoxy]butanoyl) dodecanedioic acid dihydrazide
N'-(3-Carboxypropionyl) O-(1,3-dimethyl-3-[t-butylperoxy]butyl)carbazate, also known by the alternate name 1,3-Dimethyl-3-(t-butylperoxy)butyl 3-(3-carboxypropionyl)carbazate
O-(1,3-Dimethyl-3-[t-butylperoxy]butyl) N-phthalimido carbamate
O-(1,3-Dimethyl-3-[t-butylperoxy]butyl) N-([3,4,5,6-tetrabromo]phthalimido) carbamate
O-(1,3-Dimethyl-3-[t-butylperoxy]butyl) N-[(3,4,5,6-tetrachloro]phthalimido) carbamate
O-(1,3-Dimethyl-3-[t-butylperoxy]butyl) N-([4-carboxy]phthalimido) carbamate
O-(1,3-Dimethyl-3-[t-butylperoxy]butyl) N-([4-nitro]phthalimido) carbamate
O-(1,3-Dimethyl-3-[t-butylperoxy]butyl) N-maleimido carbamate
O-(1,3-Dimethyl-3-[t-butylperoxy]butyl) N-succinimido carbamate
O-(1,3-Dimethyl-3-[t-butylperoxy]butyl) N-(2-decylsuccinimido) carbamate
O-(1,3-Dimethyl-3-[t-butylperoxy]butyl) N-(2-[1-decenyl]succinimido) carbamate
O-(1,3-Dimethyl-3-[2-ethylhexanoylperoxy]butyl) N-maleimido carbamate
O-(1,3-Dimethyl-3-[2-ethylhexanoylperoxy]butyl) N-succinimido carbamate
O-(1,3-Dimethyl-3-[t-butylperoxy]butyl) N-(2-succinimidoethyl) carbamate
O-(1,3-Dimethyl-3-[t-butylperoxy]butyl) N-(2-phthalimidoethyl) carbamate
N-Succinimido 4,4-di-(t-butylperoxy)pentamide
N-Phthalimido 3,3-di-(t-butylperoxy)butanamide
N-(1-Methyl-1-[4-(1-methyl-1-[t-butylperoxy]ethyl)-phenyl]ethyl) phthalimide
N-(1-Methyl-1-[4-(1-methyl-1-[t-butylperoxy]ethyl)-phenyl]ethyl) succinimide N-(1-Methyl-1-[4-(1-methyl-1-[t-butylperoxy]ethyl)-phenyl]ethyl) maleimide 3-(1,4,4,6-Tetramethyl-2,3,7-trioxacycloheptyl)-N'-(3-carboxypropionyl)propionhydrazide 1-(1-Amino-1-methylethyl)-4-(1-methyl-1-[t-butylperoxy]ethyl)benzene hydrochloride salt 1-(1-Amino-1-methylethyl)-4-(1-methyl-1-[t-butylperoxy]ethyl)benzene p-toluenesulfonic acid salt 1,3-Dimethyl-3-(t-butylperoxy)butyl carbazate hydrochloride salt Performance Additive Derivatives Novel performance additive derivatives of the AHP's of the present invention for polymers can be synthesized by reacting the AHP's with performance additive compounds that are co-reactive with the amino functional group of the AHP's. As used herein, the term "performance additive" relates to a compound or composition having functional groups or moieties which enhance the performance of polymers or other compounds or compositions to which they are added. For example, the performance and use of polymers will be enhanced by ultraviolet ("UV") stabilizers, hindered amine light stabilizers ("HALS"), and flame retardants, among others. Bases useful in these reactions include the bases listed above.

Co-reactive performance additive compounds which may be reacted with the AHP's of the present invention include, for example, 2-cyano-3,3-diphenylpropenoyl chloride, 2-(4-benzoyl-3-hydroxyphenoxy)ethyl chloroformate, 2-(4-benzoyl-3-hydroxyphenoxy)propyl chloroformate, (4-benzoyl-3-hydroxyphenoxy)acetyl chloride, 2-(4-benzoyl-3-hydroxyphenoxy)propionyl chloride, 2-(4-[2H-benzotriazol-2-yl]-3-hydroxyphenoxy)ethyl chlorocarbonate, 2-(3-[2H-benzotriazol-2-yl]-4-hydroxyphenoxy)ethyl chlorocarbonate, 4-(2H-benzotriazol-2-yl)-3-hydroxyphenoxyacetyl chloride, 3-(2H-benzotriazol-2-yl)-4-hydroxyphenoxyacetyl chloride, dimethyl 4-(2-chlorocarbonyloxyethoxy)benzylidenemalonate, diethyl 4-(2-chlorocarbonyloxyethoxy)benzylidenemalonate, dipropyl 4-(chlorocarbonylmethoxy)benzylidenemalonate, 2,2,6,6-tetramethyl-4-piperidinyl chloroformate and 2,2,6,6-tetramethyl-4-piperidone.

Non-limiting examples of the performance additive derivatives of the novel AHP's include the following:

AMP-Performance Additive Derivatives UV Stabilizer-Peroxides 1-(2-Cyano-3,3-diphenylpropenoyl)-2-(4,4-di-[t-amylperoxy]pentanoyl)hydrazine O-(1,3-Dimethyl-3-[t-butylperoxy]butyl) N'-(2-[4-benzoyl-3-hydroxyphenoxy]ethoxycarbonyl) carbazate O-(2-[4-(2,2-Di[methoxycarbonyl]ethenyl)phenoxy]ethyl) N'-(4,4-di-[t-amylperoxy]pentanoyl) carbazate HALS-Peroxides 2,2,6,6-Tetramethyl-4-piperidinyl-(4,4-di-[t-butylperoxy]pentanoyl)hydrazone O-(2,2,6,6-Tetramethyl-4-piperidinyl) N'-(1,3-dimethyl-3-[t-butylperoxy]butyl) carbazate O-(2,2,6,6-Tetramethyl-4-piperidinyl) N-(2-[1,3-dimethyl-3-(t-butylperoxy)butoxycarbonylamino]ethyl) carbamate Coupled Peroxide Derivatives Novel coupled peroxide derivatives of the AHP's of the present invention can be synthesized by reacting the AHP's with coupling agents that are co-reactive with the amino functional groups of the AHP's. Optional bases useful in these reactions include the bases listed above. Reaction conditions are those which affect coupling of the AHP's and are well known to those skilled in the art or would be readily discernible based on the disclosure herein.

The coupled peroxide derivatives within Structure A of the present invention reduce the volatility of the peroxides, rendering them less fugitive in polymeric compositions. The coupled peroxides, which may include polyperoxides, can be used to make higher molecular weight polymers when used as free radical initiators.

Coupling agents which may be reacted with the AHP's of the present invention include, for example, sulfuryl chloride; phosgene; diacid chlorides, such as oxalyl chloride, succinoyl chloride, adipoyl chloride, 1,12-dodecanedioyl chloride and terephthaloyl chloride; bischloroformates such as ethylene glycol bischloroformate, diethylene glycol bischloroformate, neopentyl glycol bischloroformate and Bisphenol A bischloroformate; diisocyanates such as hexamethylene diisocyanate, toluene diisocyanate, 4,4'-methylene bis(phenylisocyanate) and isophorone diisocyanate; and dianhydrides such as pyromellitic dianhydride, benzophenone dianhydride and ethylene bis(anhydrotrimellitate).

Non-limiting examples of the coupled peroxide derivatives of the novel AHP's include the following:

Coupled Peroxides

N,N'-Bis(2-[1,3-dimethyl-3-(t-butylperoxy)butoxycarbonylamino]ethyl) pyromellitic diimide N,N'-Bis(4,4-di-[t-butylperoxy]pentamido) pyromellitic diimide N,N'-Di-(1-methyl-1-[4-(1-methyl-1-[t-butylperoxy]ethyl)phenyl]ethyl) urea N,N'-Bis(1-methyl-1-[4-(1-methyl-1-[t-butylperoxy]ethyl)phenyl]ethyl) pyromellitic diimide N,N'-Di-(1-methyl-1-[4-(1-methyl-1-[t-butylperoxy]ethyl)phenyl]ethyl) succinamide N,N'-Di-(1-methyl-1-[4-(1-methyl-1-[t-butylperoxy]ethyl)phenyl]ethyl) terephthalamide Sequential Peroxide Derivatives A sequential peroxide is defined as a compound with two or more peroxide groups having different half-lives which decompose at different temperatures. They are particularly useful in making peroxy polymers, that is, polymers with peroxide end groups. Lower temperatures decompose the shorter half-life peroxide to yield free radicals and initiate polymerization. The peroxide group with the longer half-life forms block copolymers at higher temperatures. If a homopolymer is made from the sequential (di)peroxide, it can have higher molecular weight than if two individual peroxides having the half-life characteristics of the sequential (di)peroxide are used to make the homopolymer. The sequential (di)peroxide is also advantageously less volatile than two individual peroxides having the half-life characteristics of the sequential (di)peroxide.

Novel sequential peroxide derivatives of the AHP's of the present invention can be synthesized by reacting the AHP's of this invention with peroxy compounds having decomposition kinetics different than those of the AHP's and which are co-reactive with the amino functional groups of the AHP's. Optional bases useful in these reactions include the bases listed above. Reaction conditions are those which affect reaction of the AHP's and the co-reactive peroxy compounds and are well known to those skilled in the art or would be readily discernible based on the disclosure herein.

Co-reactive peroxy compounds which may react with the AHP's of the present invention include, for example, 2-(t-butylperoxycarbonyl)benzoyl chloride, 3-(t-butylperoxycarbonyl)propionyl chloride, 4-(t-amylperoxycarbonyl)butyryl chloride, 4,4-di-(t-butylperoxy)pentyl chloroformate, 1,3-dimethyl-3-(t-butylperoxy)butyl chloroformate, 3-methyl-3-(t-butylperoxy)butyl chloroformate, 1,3-dimethyl-3-(t-amylperoxy)butyl chloroformate, 1,3-dimethyl-3-(2-ethylhexanoylperoxy)butyl chloroformate, 1,3-dimethyl-3-(neoheptanoylperoxy)butyl chloroformate, di-(1,1-dimethyl-3-chlorocarbonyloxybutyl) peroxide, di-(1,1-dimethyl-3-chlorocarbonyloxypropyl) peroxide and 4,4-di-(t-butylperoxy)pentanoic acid anhydride.

Non-limiting examples of sequential peroxide derivatives of the novel AHP's include the following:

Sequential Peroxides

O-(1,3-Dimethyl-3-[t-butylperoxy])butyl) N'-(3-[t-butylperoxycarbonyl]propionyl) carbazate O-(1,3-Dimethyl-3-[t-butylperoxy]butyl) N'-(2-[t-butylperoxycarbonyl]benzoyl) carbazate O-(1,3-Dimethyl-3-[2-ethylhexanoylperoxy]butyl) N'-(1,3-dimethyl-3-[t-butylperoxy]butoxycarbonyl) carbazate O-(1,3-Dimethyl-3-[t-butylperoxy]butyl) N'-(3,3-di-[t-butylperoxy]butanoyl) carbazate O-(1,3-Dimethyl-3-[t-butylperoxy]butyl) N'- (4,4-di-[t-amylperoxy]pentanoyl) carbazate Polymeric Peroxide Derivatives Novel polymeric peroxide derivatives of the AHP's of the present invention can be synthesized by reacting the AHP's of this invention with anhydride polymers or copolymers, lower alkyl hydrogen maleate polymers or copolymers, lower alkyl hydrogen fumarate polymers or copolymers, and lower alkyl acrylate and methacrylate copolymers in which at least one of the co-momomers is acrylic acid, methacrylic acid, maleic acid or fumaric acid.

In general, any additional polymer or copolymer of ethylenic monomers and containing cyclic anhydride groups, either on the polymer backbone or grafted side chains, is suitable for attachment of the AHP's to form the peroxy polymer derivatives of the AHP's of this invention. Due to cost and ease of preparation, the anhydride containing polymers are preferably polymers or polymers of maleic anhydride, although polymers or copolymers of other cyclic anhydrides may be used to form the polymeric peroxide derivatives of the AHP's of the present invention.

Suitable anhydride containing copolymers useful for employment in this invention include but are not limited to: (a) styrene-maleic anhydride copolymers; (b) alternating copolymers of maleic anhydride and alpha-olefins; (c) copolymers of alkyl vinyl ethers and maleic anhydride; (d) maleic anhydride modified polyolefins; (e) maleic anhydride adducts of hydrogenated polymers or copolymers; (f) maleic anhydride adducts of EPDM; and (g) other anhydride copolymers.

The styrene/maleic anhydride copolymers employed in this invention are a general class of compounds consisting of the alternating copolymers of styrene and maleic anhydride, or the non-equimolar copolymers containing less than about 50 mole percent of the anhydride monomer. The styrene may be replaced in whole or in part by other vinylaromatic monomers such as alpha-methylstyrene, nuclear methylstyrenes, ethylstyrene, isopropylstyrene, t-butylstyrene, chlorostyrenes, dichlorostyrenes, bromostyrenes, dibromostyrenes, vinylnaphthalene and the like. Similarly, the maleic anhydride can be replaced in whole or in part by another alpha, beta-unsaturated cyclic dicarboxylic acid anhydride such as itaconic, aconitic, citraconic, mesaconic, chloromaleic, bromomaleic, dichloromaleic, dibromomaleic, phenylmaleic and the like. The preferred alpha, beta-unsaturated cyclic anhydride is maleic anhydride. The copolymer may also contain a termonomer, such as a $C_1$ to $C_3$ alkyl acrylate or methacrylate, acrylonitrile, methacrylonitrile, acrylamide, methacrylamide, acrylic acid or methacrylic acid.

Suitable copolymers may be prepared by any of the several methods available for the preparation of styrene-maleic anhydride copolymers or they may be purchased commercially. Non-equimolar copolymers may be prepared by solution polymerization directly from the respective monomers by the incremental addition of the reactive monomer as taught by U.S. Pat. No. 2,971,939; by a continuous recycle polymerization process, such as described in U.S. Pat. Nos. 2,769,804 and 2,989,517; by the suspension polymerization process described in U.S. Pat. No. 3,509,110 or by numerous known variations. The disclosure of each of these patents is hereby incorporated herein by reference.

Also suitable are the rubber-modified copolymers where 5 to 40 percent by weight of one of the known elastomers has been incorporated into the vinylaromatic-alpha, beta-unsaturated dicarboxylic acid anhydride copolymer. The elastomers may be incorporated into the anhydride copolymers by blending, mixing or copolymerizing the monomers in the presence of the rubber.

Suitable rubbers or elastomers include conjugated 1,3-diene rubbers, styrene/diene copolymer rubbers, acrylonitrile/diene copolymer rubbers, ethylene/propylene copolymer rubbers, ethylene/propylene/diene terpolymer rubbers, acrylate/diene copolymer rubbers, and mixtures thereof.

Preferred rubbers are diene rubbers such as homopolymers of conjugated dienes such as butadiene, isoprene, chloroprene, and piperylene and copolymers of such dienes with up to 50 mole percent of one or more copolymerizable mono-ethylenically unsaturated monomers, such as styrene, substituted styrenes, acrylonitrile, methacrylonitrile and isobutylene.

Preferably, the elastomers are incorporated into the monomer mixture prior to polymerization using, for example, the method of U.S. Pat. Nos. 4,097,551 or 4,486,570 in which a mixture of at least two rubbery additives is present during the polymerization. The disclosures of these patents are hereby incorporated herein by reference.

Particularly suitable for use are the non-equimolar polymers of styrene and maleic anhydride designated Dylark TM copolymers, commercially available from ARCO Chemical Company division of Atlantic Richfield Company. Suitable Dylark TM copolymers include those of the 200 series and the 300 series and Dylark TM 700 copolymer. Those copolymers designated Dylark TM 250, Dylark TM 350 and Dylark TM 700 are impact modified.

The SMA TM resins available from ARCO Chemical Company are low molecular weight styrene/maleic anhydride copolymers (MW 700–1900), for example. SMA TM 1000, 2000 and 3000 are also useful in this invention.

Also suitable are the styrene/maleic anhydride copolymers or rubber modified styrene/maleic anhydride copolymers where a portion of the maleic anhydride groups are converted to maleimide groups or N-substituted maleimide groups. The partially imidated copolymers can be prepared by treating the styrene/maleic anhydride copolymer with a primary amine in a post polymerization step as described in U.S. Pat. No. 3,998,907 or during the polymerization as described in U.S. Pat. No. 4,381,373, the disclosures of which are hereby incorporated by reference. The molar ratio of the amine to the maleic anhydride in the copolymer should be less than 0.8 to allow attachment of the peroxide groups via the amino or hydrazino groups of the AHP's. The formation of the maleimide groups that do not contain peroxide groups may be formed before, during or after the formation of the maleamic acid or maleimide groups containing peroxide groups. Suitable amines for this purpose are ammonia, primary alkyl amines and primary aryl amines.

The styrene/maleic anhydride copolymer may optionally contain a termonomer such as a $C_1$ to $C_3$ alkyl acrylate or methacrylate, acrylonitrile, methacrylonitrile, acrylamide, methacrylamide, acrylic acid or methacrylic acid. Rubber modified terpolymers of styrene, maleic anhydride and lower alkyl ($C_1$ to $C_3$) methacrylates are described in U.S. Pat. No. 4,341,695. The polymeric composition is conveniently prepared by dissolving the rubber in a solution of the monoalkenyl aromatic component and the methacrylate ester in a suitable solvent and then polymerizing the solution with the anhydride component in the manner described in, for example, U.S. Pat. Nos. 2,971,939, 3,336,267 and 3,919,354. The disclosures of the latter two patents are hereby incorporated herein by reference.

The Cadon TM resins (Monsanto Chemical Company) are a commercial series of styrene/maleic anhydride polymer alloys with acrylonitrile/butadiene/styrene (ABS). Rubber-modified versions are also available. These resins are also suitable for this invention.

Also suitable are the rubber modified styrene maleic anhydride resins described in U.S. Pat. No. 4,522,983 where a minor amount of a nuclear substituted methylstyrene is included in the composition. The disclosure of this patent is hereby incorporated herein by reference.

The styrene/maleic anhydride polymers may be further modified by copolymerizing the monomers in the presence of other monomers. In addition to the acrylates, methacrylates, acrylonitrile and methacrylonitrile previously mentioned, other suitable monomers include the ethylenically unsaturated carboxylic acids, preferably acrylic and methacrylic acids, acrylamide and methacrylamide $C_1$ to $C_6$ alkyl acrylates or methacrylates, dialkylamino $C_1$ to $C_6$ alkyl acrylates or methacrylates, such as dimethylaminoethyl acrylate or methacrylate, and vinyl esters derived from saturated carboxylic acids of 2 to 22 carbon atoms, such as vinyl acetate or vinyl propionate.

Further modification of the styrene/maleic anhydride copolymers can be accomplished by carrying out the copolymerization in the presence of crosslinking monomers having two or more ethylenically unsaturated double bonds such as divinylbenzene, 1,4-butadiene, divinyl ether, ethylene glycol dimethacrylate, butanediol dimethacrylate, triallyl cyanurate and similar type compounds. The crosslinking monomers are employed in amounts of from 0.01 to 5, preferably from 0.1 to 2 mole percent based on maleic anhydride.

Alternating copolymers of maleic anhydride and alpha-olefins are well known in the art, as exemplified by U.S. Pat. Nos. 3,553,177, 3,560,455, 3,560,456 and 3,560,457. Each of these patents describes a copolymer of maleic anhydride with a specific alpha-olefin such as $C_{12}$ to $C_{30}$ alpha-olefins. The copolymers of $C_6$ to $C_{10}$ alpha-olefins are known as disclosed by U.S. Pat. No. 3,488,311. Terpolymers of maleic anhydride and at least one lower alpha-olefin and at least one higher alpha-olefin are also known, as disclosed by U.S. Pat. No. 4,358,573. The disclosures of the patents referred to in this paragraph are hereby incorporated herein by reference.

The alternating copolymers may be prepared by conventional polymerization processes including those described in U.S. Pat. Nos. 3,553,177, 3,560,455, 3,560,456, 3,560,457 and 3,488,311, the disclosures of which are hereby incorporated herein by reference. PA-18 TM (Chevron Chemical Company) is an example of a commercially available alternating copolymer of maleic anhydride and octadecene-1.

Also suitable for this invention are the terpolymers disclosed in U.S. Pat. Nos. 4,522,992 and 3,723,375, the disclosures of which are hereby incorporated herein by reference. These are basically terpolymers of cyclic alpha, beta-unsaturated dicarboxylic acid anhydrides, aromatic mono-alkenyl monomers and higher 1-alkenes. Preferably, they are terpolymers of styrene, maleic anhydride and alpha-olefins having 10 or more carbon atoms. Both pure alkenes and mixed alkenes can be utilized in preparing the terpolymers.

Alternating polymers of alkyl vinyl ethers and maleic anhydride are readily prepared in bulk or solution using free radical initiators (e.g. lauroyl peroxide) as disclosed in British Patent 1,117,515, the disclosure of which is hereby incorporated herein by reference. Low, medium and high molecular weight grades are commercially available. Commercial grades include the Gantrez TM resins (GAF Corp.). Suitable alkyl vinyl ethers for this invention include methyl, ethyl, propyl, isopropyl, n-butyl, isobutyl, amyl, isoamyl, hexyl, heptyl, octyl, 2-ethylhexyl, nonyl, decyl, dodecyl, hexadecyl and octadecyl vinyl ethers.

The maleic anhydride modified polyolefins employed in this invention have the general formula:

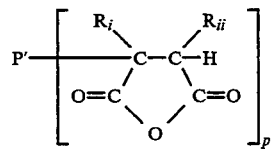

where $R_i$ and $R_{ii}$ are as previously defined and $P'$-represents an olefin polymer residue which is based on a preponderance of ethylene, propylene or 1-butene, and having a valence of p. It can be either a high or low density polyethylene residue, a polypropylene residue or a residue of a copolymer of ethylene with 1-butene, a residue of a copolymer of ethylene and propylene, a residue of a propylene-butene copolymer or a residue of such a propylene copolymer with an olefin having up to about six carbon atoms.

The maleic anhydride-modified polyolefins are known materials containing about 0.2 to 9% by weight of combined maleic anhydride, preferably about 2 to 5%. In fact, one embodiment of these materials is a commercially available product, Hercoprime TM by Hercules Incorporated. Polyethylene or polypropylene modified with maleic anhydride is available commercially as Plexar TM from Enron Chemical Co. Any polymer or copolymer of ethylene, propylene, or 1-butene can be modified via the maleic anhydride moiety to form the substrate molecule, including polyethylene, polypropylene, ethylene/propylene copolymer, propylene/butene-1 copolymer, or butene-1/ethylene copolymer. The most frequently encountered and the preferred maleic anhydride modified polyolefin is that based on polypropylene.

The preparation of maleic anhydride modified polypropylene is described in, inter alia, U.S. Pat. No. 3,483,276, the disclosure of which is hereby incorporated herein by reference. Briefly, the preparation consists of treating the olefin polymer with a material or by means which will induce the formation of active, free radical sites thereof with which maleic anhydride can react. Active centers can be induced, e.g. by subjecting the polymer to the action of high energy ionizing radiation such as gamma rays, X-rays, or high speed electrons; by contacting it, either as a solid or a solution in a solvent, with a free radical initiator, such as dibenzoyl peroxide, dilauroyl peroxide, dicumyl peroxide or t-butyl peroxybenzoate; or by simply milling it in the presence of air. The preferred method is the reaction of the polyolefin with maleic anhydride in solvent solution in the presence of a free radical initiator.

The olefin polymer based maleamic acids and maleimides of the invention are prepared by graft modifying the appropriate polymer backbone with a maleic anhydride and thereafter reacting the anhydride modified olefin polymer with the AHP's containing primary amino or hydrazide functionalities. A less preferred method is to modify the appropriate polymer backbone with N-(peroxide substituted)-maleimides of formula:

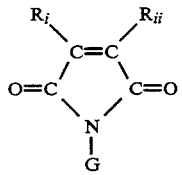

where $R_i$, $R_{ii}$ and G are as previously defined.

The graft modification of EPDM by maleic anhydride in the presence of dicumyl peroxide and benzoyl peroxide is described by DeVito and co-workers (G. DeVito, N. Lanzetta, G. Maglio, M. Malinconico, P. Musta, R. Palumbo, J. Polym. Sci., Polym. Chem., Ed., 22, pp. 1335–47 (1984)), the disclosure of which is hereby incorporated herein by reference.

U.S. Pat. No. 4,506,056, the disclosure of which is hereby incorporated herein by reference, describes a process for grafting maleic anhydride onto molten polymers or polymers using a free radical catalyst in which crosslinking or degradation of the polymers is controlled or eliminated in the presence of scavengers which inhibit the homopolymerization of maleic anhydride.

The maleic anhydride adduct polymers useful in this invention are polymeric products containing pendant succinic anhydride groups which are formed by reacting maleic anhydride with hydrogenated polymers of conjugated dienes or hydrogenated copolymers of conjugated dienes and vinyl aromatic hydrocarbons containing a residual unsaturation level of from 0.5 to 20 percent of their original unsaturation level prior to hydrogenation. The reaction which is conducted by heating a mixture of the maleic anhydride and hydrogenated polymer or copolymer containing residual unsaturation proceeds by means of a reaction mechanism referred to as an "ene" reaction well known to those skilled in the art. The maleic anhydride adds to the unsaturation of the polymer to form the polymer product containing the pendant succinic anhydride groups. By virtue of the pendant anhydride groups, this polymer can be reacted with peroxides containing primary amino or hydrazide groups to form the polymer bound peroxides of this invention.

The amounts of maleic anhydride employed in the reaction can vary considerably depending on the specific nature of the hydrogenated polymer and the properties desired in the final product. In general, the amount of maleic anhydride employed may range from 0.1 to about 25 percent by weight based on the total weight of maleic anhydride and hydrogenated polymer with a preferred amount being from 0.2 to 5 percent by weight.

Various polymers of conjugated dienes and copolymers of conjugated dienes and vinyl aromatic hydrocarbons may be hydrogenated for use in preparing the maleic anhydride adduct component of the compositions of the invention. Polymers of conjugated dienes which may be hydrogenated include polymers derived from one or more conjugated diene monomers. Thus, polymers derived from a single conjugated diene such as, for example, 1,3-butadiene (i.e. a homopolymer) or polymers derived from two or more conjugated dienes such as, for example, 1,3-butadiene and isoprene or 1,3-butadiene and 1,3-pentadiene (i.e. a copolymer), and the like, may be utilized. Copolymers which may be hydrogenated include random copolymers of conjugated dienes and vinyl aromatic hydrocarbons and block copolymers of conjugated dienes and vinyl aromatic hydrocarbons which exhibit elastomeric properties.

Examples of polymers of conjugated dienes and random and block copolymers of conjugated dienes and vinyl aromatic hydrocarbons that can be utilized in the invention are described in European Patent Publication No. 103,148, published Mar. 21, 1984, based on European Patent Application No. 83107732.6, filed May 8, 1983. Many of these polymers and copolymers are commercially available and they may be hydrogenated by a variety of well established processes. Suitable hydrogenation processes are described in U.S. Pat. Nos. 3,113,986 and 4,226,952. The disclosures of the European Patent Application and the U.S. Patents referred to in this paragraph are hereby incorporated herein by reference.

The maleic anhydride adduct is prepared by a relatively uncomplicated process which does not require complex copolymerization or grafting procedures. It can be prepared by first forming a homogeneous mixture or solution of the maleic anhydride and the hydrogenated polymer or copolymer containing residual unsaturation and then reacting the resultant mixture or solution under appropriate conditions of time and temperature. Examples of appropriate reaction conditions are given in European Patent Publication No. 103,148.

The maleic anhydride adducts of EPDM are also suitable maleic anhydride polymers for attachment of reactive peroxide groups. They are prepared by the thermal addition of maleic anhydride to elastomeric copolymers of ethylene and propylene which have a substantially saturated hydrocarbon backbone chain and unsaturated hydrocarbon side-chains. The preparation of these adducts is described in U.S. Pat. No. 3,884,882, the disclosure of which is hereby incorporated herein by reference.

Examples of other anhydride copolymers that are suitable for use in this invention for attaching peroxide groups to polymer backbones via amic acid or imide formation include the following non-limiting list:
1) vinyl acetate/maleic anhydride copolymer;
2) ethylene/vinyl acetate/maleic anhydride terpolymer;
3) isobutylene/maleic anhydride copolymer;
4) graft polyols containing styrene/maleic anhydride copolymer in the grafted chain;
5) styrene/maleic anhydride-2,4,6-tribromophenyl acrylate terpolymer;
6) maleic anhydride/divinylbenzene/styrene terpolymer;
7) ethylene/maleic anhydride/styrene graft copolymer;
8) methyl methacrylate/maleic anhydride copolymers;
9) butyl methacrylate/maleic anhydride/styrene terpolymer; and
10) ethylene/maleic anhydride copolymers (available from Monsanto Chemical Company).

Other suitable maleic anhydride copolymers include the terpolymers of anhydrides, aromatic mono-alkenyl monomers and higher 1-alkenes described in U.S. Pat. No. 4,522,992, the tribromophenyl acrylate/epichlorohydrin/maleic anhydride/styrene copolymer described in U.S. Pat. No. 4,108,943, and the methyl methacrylate/maleic anhydride/styrene copolymers disclosed in Japanese Patent Publications 59,221,314 and 59,221,315, both dated Dec. 12, 1984, relating to Japanese Patent Applications 83/95,070 and 83/95,071, respectively, both filed May 31, 1983, abstracted in Chem. Abst. (102:150317x and 150318y), divinyl ether/maleic anhydride copolymers from Adica Labs (Pivan), a polybutadiene/polystyrene/maleic anhydride terpolymer referred to as Ricon ™ 184/MA, a product of Colorado Chemical Specialties, Inc., and ethylene/vinyl acetate copolymer grafted with maleic anhydride such as Modic E 310K a product of Mitsubishi Chemical Industries Co.

Poly(maleic anhydride) such as Belcene, a product of Ciba-Geigy Corp., is also suitable in this invention.

Anhydride polymers containing glutaric anhydride units (i.e., where t=1), as opposed to those containing succinic anhydride units (i.e., where t=0), can also be used in the practice of this invention. Such polymeric anhydrides (i.e., those with glutaric anhydride units) are available from polymers and polymers of acrylic acid and methacrylic acid by heating under dehydrating conditions, with or without a catalyst (European Patent Publication No. 76,691, published Apr. 13, 1983, based on European Patent Application 82350285.7, filed Oct. 5, 1982), or from homopolymerizing or copolymerizing acrylic acid anhydride or methacrylic acid anhydride under a variety of conditions.

The polymeric amic acid derivatives of the AHP's that are derived from cyclic anhydride-containing polymers and copolymers can be prepared by reacting the AHP's and the cyclic anhydride-containing polymers and copolymers in solution, at temperatures in the range of about 0° C. to about 180° C., followed by isolation of the polymeric amic acid peroxides. The polymeric imide derivatives of the AHP's can be prepared from the above polymeric amic acid peroxides or mixtures of the AHP's and anhydride-containing polymers and copolymers by azeotroping water from solution or by reacting with effective amounts of, preferably, acetic anhydride and sodium acetate in solution, at temperatures in the range of about 40° C. to about 180° C., followed by isolation of the polymeric imide peroxides (British Patent 1,307,409, Example 3). A non-limiting list of solvents useful in these reactions include aromatic solvents, such as benzene, toluene, xylenes, mesitylene, ethyl benzene, cumene and others, and dimethyl sulfoxide, dimethylformamide, gamma-butyrolactone and propylene carbonate.

Alternately, the polymeric amic acid derivatives of the AHP's can be prepared by reacting the anhydride containing polymers with AHP's in polymer mixing equipment such as extruders, etc., at temperatures beginning in the range of the softening point of the anhydride containing polymer, about 80° C., to about 180° C., no solvent being used. The polymeric imide derivatives of the AHP's are more difficult to prepare in polymer mixing equipment owing to significant thermal decomposition of the peroxide groups at the temperatures required to dehydrate and cyclize the amic acid group to the imide group, i.e., 180° C. to 300° C. It is unimportant to form imide linkage in polymer mixing equipment, since the amic acid linkage of the peroxide group to the polymer is just as effective as the imide linkage in applications of polymeric peroxides. Once the peroxide group of the polymeric amic acid peroxide has been used (decomposed) in an application, the amic acid linkages of the non-peroxidic polymeric product can be converted at the higher temperatures to the more thermally stable imide linkages. However, owing to lower solution viscosities of peroxy polymers with imide linkages compared to those with amic acid linkages, the polymeric imide derivatives of the AHP's are preferred, from the handling point of view.

Suitable lower alkyl hydrogen maleate copolymers useful for preparation of the novel polymeric peroxide derivatives from the non-polymeric AHP's of Structure A include copolymers such as ethylene/alkyl acrylate/alkyl hydrogen maleate or ethylene/alkyl methacrylate/alkyl hydrogen maleate terpolymers.

Other novel polymeric peroxide derivatives of the AHP's of this invention can be synthesized by reacting the AHP's of this invention with polymers possessing pendant acid groups (formation of polymers with pendant ammonium-peroxide or hydrazinium-peroxide salts or pendant amide-peroxide or hydrazide-peroxide groups), polymers possessing pendant isocyanate groups (formation of polymers with pendant urea-peroxides or pendant semi-carbazide-peroxide groups), polymers possessing pendant epoxy groups (formation of polymers with pendant hydroxyalkylamino- or hydroxyalkyl-hydrazino-peroxide groups), polymers with pendant halide (bromide or chloride) groups (formation of polymers with pendant amino-peroxide or hydrazino-peroxide groups), polymers possessing pendant aldehyde or ketone functions (formation of polymers with pendant Schiff base- (imino-) peroxide or hydrazone-peroxide groups), polymers possessing pendant ester or carboxylic acid chloride groups (formation of polymers with pendant amide-peroxide or hydrazide-peroxide groups), polymers possessing pendant chloroformate groups (formation of polymers with pendant carbamate-peroxide or carbazate-peroxide groups) or polymers possessing pendant oxazoline groups (formation of polymers with pendant amidoethyleneaminoperoxide or amidoethylenehydrazino-peroxide groups).

Still other novel polymeric peroxide derivatives of the AHP's of this invention can be synthesized by reacting the AHP's of this invention with polymers possessing the above named pendant groups as end-groups instead of pendant groups. Polymers with corresponding peroxide end-groups are formed.

Utility of The AHP's Polymerization of Ethylenically Unsaturated Monomers

The novel AHP's of Structure A of this invention were found to be effective initiators with respect to efficiency (reduced initiator requirements, etc.) in the free-radical polymerizations of ethylenically unsaturated monomers at suitable temperatures and pressures. Ethylenically unsaturated monomers include olefins, such as ethylene, propylene, styrene, alpha-methylstyrene, p-methylstyrene, chlorostyrenes, bromostyrenes, vinylbenzyl chloride, vinylpyridine and divinylbenzene; diolefins, such as 1,3-butadiene, isoprene and chloroprene; vinyl esters, such as vinyl acetate, vinyl propionate, vinyl laurate, vinyl benzoate and divinyl carbonate; unsaturated nitriles, such as acrylonitrile and methacrylonitrile; acrylic acid and methacrylic acid and their anhydrides, esters and amides, such as acrylic acid anhydride, methyl, ethyl, n-butyl, 2-hydroxyethyl, lauryl and 2-ethylhexyl acrylates and methacrylates, and acrylamide and methacrylamide; maleic anhydride and itaconic anhydride; maleic, itaconic and fumaric acids and their esters; vinyl halo and vinylidene dihalo compounds, such as vinyl chloride, vinyl bromide, vinyl fluoride, vinylidene chloride and vinylidene fluoride; perhalo olefins, such as tetrafluoroethylene, hexafluoropropylene and chlorotrifluoroethylene; vinyl ethers, such as methyl vinyl ether, ethyl vinyl ether and n-butyl vinyl ether; allyl esters, such as allyl acetate, allyl benzoate, allyl ethyl carbonate, triallyl phosphate, diallyl phthalate, diallyl fumarate, diallyl glutarate, diallyl adipate, diallyl carbonate diethylene glycol bis(allyl carbonate) (i.e., ADC); acrolein; methyl vinyl ketone; and mixtures thereof.

Temperatures of about 0° C. to about 250° C., preferably about 30° C. to about 200° C., and AHP levels (on a pure basis) of about 0.002 to about 3%, preferably about 0.002 to about 1% by weight based on monomer, are normally employed in conventional polymerizations and copolymerizations of ethylenically unsaturated monomers.

The AHP's of this invention can be used in combination with other free-radical initiators including, for example, peroxyesters, such as t-butyl peroxypivalate, t-butyl peroxy-2ethylhexanoate, t-butyl peroxyacetate, t-amyl peroxypivalate, t-butyl peroxyneodecanoate, t-amyl peroxyneodecanoate, 1,1,3,3-tetramethylbutyl peroxyneodecanoate and alpha-cumyl peroxyneodecanoate; dialkyl peroxydicarbonates, such as di-n-propyl, diisopropyl, di-(sec-butyl), dicyclohexyl, di-(4-t-butylcyclohexyl), di-(2-phenoxyethyl), di-(2-ethylhexyl) and dihexadecyl peroxydicarbonates; acyl alkylsulfonyl peroxides, such as acetyl cyclohexylsulfonyl peroxide and acetyl sec-heptylsulfonyl peroxide; diacyl peroxides, such as dibenzoyl peroxide, didodecyl peroxide, diisobutyryl peroxide and di-(2-methylpentanoyl)peroxide; diperoxyketals such as, 2,2-di-t-butylperoxy)butane, 2,2-di-(t-butylperoxy)heptane, ethyl 3,3-di-(t-butylperoxy)butyrate, 1,1-di-(t-butylperoxy)-3,3,5-trimethylcyclohexane, 1,1-di-(t-butylperoxy)cyclohexane; and 1,1-di(t-amylperoxy)cyclohexane; monoperoxycarbonates such as OO-t-butyl O-isopropyl monoperoxycarbonate and OO-t-butyl O-(2-ethylhexyl) monoperoxycarbonate; dialkyl peroxides, such as 2,5-dimethyl-2,5-di-(t-butylperoxy)hexane; and azo compounds, such as azo-bis(isobutyronitrile), 2-t-butylazo-2-cyano-4-methoxy-4-methylpentane and 1-t-butylazo-1-cyanocyclohexane. Using the AHP's in combination with these initiators adds flexibility to the processes of polymer producers and allows them to "fine tune" their polymerization processes. Mixtures of two or more AHP's can also be used where appropriate.

Curing of Unsaturated Polyester Resins

In the curing of unsaturated polyester resin compositions by heating at suitable curing temperatures in the presence of free-radical curing agents, the AHP's of Structure A of this invention exhibit enhanced curing activity in the curable unsaturated polyester resin compositions. Unsaturated polyester resins that can be cured by the AHP's of this invention usually include an unsaturated polyester and one or more ethylenically unsaturated monomers.

The unsaturated polyesters are, for instance, polyesters as they are obtained by esterifying at least one ethylenically unsaturated di- or polycarboxylic acid, anhydride or acid halide, such as maleic acid, fumaric acid, glutaconic acid, itaconic acid, mesaconic acid, citraconic acid, allylmalonic acid, tetrahydrophthalic acid, and others, with saturated and unsaturated di- or polyols, such as ethylene glycol, diethylene glycol, triethylene glycol, 1,2- and 1,3-propanediols, 1,2-, 1,3- and 1,4-butanediols, 2,2-dimethyl-1,3-propanediols, 2-hydroxymethyl-2-methyl-1,3-propanediol, 2-buten-1,4-diol, 2-butyn-1,4-diol, 2,4,4-trimethyl-1,3-pentanediol, glycerol, pentaerythritol, mannitol and others. Mixtures of such di- or polyacids and/or mixtures of such di- or polyols may also be used. The di- or polycarboxylic acids may be partially replaced by saturated di- or polycarboxylic acids, such as adipic acid, succinic acid, sebacic acid and other, and/or by aromatic di- or polycarboxylic acids, such as phthalic acid, trimellitic acid, pyromellitic acid, isophthalic acid and terephthalic acid. The acids used may be substituted by groups such as halogen. Examples of such suitable halogenated acids are, for instance, tetrachlorophthalic acid, tetrabromophthalic acid, 5,6-dicarboxy-1,2,3,4,7,7-hexachlorobicyclo-(2.2.1)-2-heptene and others.

The other component of the unsaturated polyester resin composition, the polymerizable monomer or monomers, can preferably be ethylenically unsaturated monomers, such as styrene, alpha-methylstyrene, p-methylstyrene, chlorostyrenes, bromostyrenes, vinylbenzyl chloride, divinylbenzene, diallyl maleate, dibutyl fumarate, triallyl phosphate, triallyl cyanurate, diallyl phthalate, diallyl fumarate, methyl acrylate, methyl methacrylate, n-butyl acrylate, n-butyl methacrylate, ethyl acrylate, and other, or mixtures thereof, which are copolymerizable with the unsaturated polyesters.

A preferred unsaturated polyester resin composition contains as the unsaturated polyester component the esterification product of 1,2-propanediol (a polyol), maleic anhydride (an anhydride of an unsaturated polycarboxylic acid) and phthalic anhydride (an anhydride of an aromatic dicarboxylic acid), as well as the monomer component, styrene.

Other types of unsaturated polyester resin compositions can be cured using the AHP's of this invention as curing catalysts. These resins, called unsaturated vinyl ester resins, include a vinyl ester resin component and one or more polymerizable monomer components. The vinyl ester resin component can be made by reacting a chloroepoxide, such as epichlorohydrin, with appropriate amounts of a bisphenol such as Bisphenol A (2,2-[4-hydroxyphenyl]propane), in the presence of a base, such as sodium hydroxide, to yield a condensation product having terminal epoxy groups derived from the chloroepoxide. Subsequent reaction of the condensation product with polymerizable unsaturated carboxylic acids, such as acrylic acid and methacrylic acid, in the presence or absence of acidic or basic catalysts well known to those skilled in the art, results in formation of the vinyl ester resin component. Normally, styrene is added as the polymerizable monomer component to complete the preparation of the unsaturated vinyl ester resin composition.

Temperatures of about 20° C. to about 200° C. and AHP levels of about 0.05% to about 5% or more by weight of curable unsaturated polyester resin composition are normally employed.

The unsaturated polyester resin compositions described above can be filled with various materials, such as sulfur, glass, carbon and boron fibers, carbon blacks, silicas, metal silicates, clays, metal carbonates, antioxidants (AO's), heat, ultraviolet (UV) and light stabilizers, sensitizers, dyes, pigments, accelerators, metal oxides, such as zinc oxide, blowing agents, nucleating agents and others.

Curing of Elastomers and Crosslinking of Thermoplastic Polymers

In the curing of elastomeric compositions, and the crosslinking of polymer compositions, by heating at suitable curing and crosslinking temperatures in the presence of free-radical curing and crosslinking agents, the AHP's of Structure A of this invention exhibit curing and crosslinking activities.

Elastomeric resin compositions that can be cured by the AHP's of this invention include elastomers such as ethylene/propylene copolymers (EPR), ethylene/-propylene/diene terpolymers (EPDM), polybutadiene (PBD), silicone rubber (SR), nitrile rubber (NR), neoprene, fluoroelastomers and ethylene/vinyl acetate copolymer (EVA).

Polymer compositions that can be crosslinked by the AHP's of this invention include olefin thermoplastics such as chlorinated polyethylene (CPE), low density polyethylene (LDPE), linear-low density polyethylene (LLDPE), and high density polyethylene (HDPE). Other crosslinkable thermoplastic polymers include PVC, polystyrene, poly(vinyl acetate), polyacrylics, polyesters, polycarbonate, etc.

Temperatures of about 80° C. to about 310° C. and AHP levels of about 0.1% to about 10%, preferably about 0.5% to about 5%, based on weight of curable elastomeric resin composition or crosslinkable olefin polymer composition, are normally employed.

The curable elastomeric resin composition or crosslinkable polymer composition optionally can be filled with the materials listed above for use with the conventional unsaturated polyester resin compositions.

Modification of Polyolefins and Other Polymers

The AHP's of Structure A of this invention exhibit polyolefin modification activity in processes for modifying polypropylene (PP) and copolymers containing more than 50% by weight of PP. Modification of the PP polymers and copolymers includes, for example, beneficial degradation of PP by reducing the polymer molecular weight and modifying the polymer molecular weight distribution.

Temperatures of about 140° C. to about 340° C. and AHP levels of about 0.01% to about 1.0% based on weight of modifiable PP polymers or copolymers are normally employed. Optionally, up to about 1% by weight of molecular oxygen can be employed as a modification co-catalyst.

Utility of Polymeric Peroxide Derivatives

The novel polymeric peroxide derivatives of the AHP's of Structure A have utility in several applications. They can be used to prepare block and graft copolymers by several techniques. A graft copolymer of the polymeric peroxide derivative can be made by using the polymeric peroxide derivative as the backbone polymer and as the initiator, and grafting monomers onto this backbone. A graft copolymer of two or more monomers that are not the same as the monomers of the polymeric peroxide of Structure A can be made by partially decomposing the polymeric peroxide first in the presence of one monomer, followed by decomposition in the presence of a second monomer, etc. The latter processes can be carried out in solution or in polymer processing equipment such as extruders. Such graft copolymers have utility in compatibilizing homopolymer and copolymer blends and alloys.

The polymeric peroxides of Structure A can also be used in reactive processing to compatibilize polymers in situ by forming block and graft copolymers in polymer processing equipment such as extruders, roll mills, etc. In the latter processes, the preformed polymeric peroxide or the polymeric peroxide formed in situ from the anhydride and one or more of the amino-containing compounds of Structure A may be used. If more than one amino containing peroxide of Structure A is reacted with an anhydride-containing polymer, the resulting polymeric peroxide can have peroxy functional groups on the backbone with a variety of activities and expanded utilities.

The polymeric peroxides can also be used to enhance the quality of interpenetrating polymer networks (IPN's) in polymer processing equipment.

Polymeric peroxides of Structure A derived from anhydride containing elastomeric polymers can be used in reactive processing to enhance the impact resistance of polymer blends.

The polymeric peroxides of Structure A also have utility as polymeric low profile/low shrink curing agents, as self-curing polymeric systems and as self degrading polymer systems.

Additionally, the polymeric peroxides of Structure A are very beneficial in polymer-peroxide master batches (i.e., polymer-peroxide composition with up to 5% or more of organic peroxides, useful in crosslinking, curing and polymer modification applications), since the peroxide functional groups are compatible with the polymer backbone (covalently attached) and cannot bloom, exude or volatilize.

The following illustrative, non-limiting examples are included for the purpose of further describing and explaining the invention.

EXAMPLE 1

Preparation of 4,4-Di-(t-butylperoxy)pentanohydrazide (I-1)

4,4-Di-(t-butylperoxy)pentanohydrazide was prepared by reacting ethyl 4,4-di-(t-butylperoxy)pentanoate with 9 molar excess of 54% aqueous hydrazine. A 3-neck flask equipped with a magnetic stirrer, a thermometer and an addition funnel was charged with 125 mL of isopropanol (IPA), 15.3 g (0.05 mole) of 99% ethyl 4,4-di-(t-butylperoxy)pentanoate and 30 g (about 0.50 mole) of 54% aqueous hydrazine at 25° C. The solution was stirred for about 20 hours at 20°-25° C. Then the reaction mass was poured into 1000 mL of water and extracted once with 300 mL of methylene chloride. After drying over 10% by weight of anhydrous magnesium sulfate and separation of the spent desiccant by filtration, the methylene chloride was removed in vacuo leaving 14.4 g of liquid product. 30 mL of pentane were added and a solid was precipitated. The solid was separated by filtration and air dried, leaving 12.2 g (83.6% of theory, uncorrected) of a white solid having a melting point (mp) of 76°-78° C. An infrared (IR) spectrum of the product showed strong carbonyl absorption bands at 1640 cm$^{-1}$ and at 1680 cm$^{-1}$ and a strong NH band at 3300 cm$^{-1}$. A DSC scan run on the product showed a peroxide decomposition exotherm at 170° C. These product data confirm that the product was 4,4-Di-(t-butylperoxy)pentanohydrazide (I-1).

In another preparation of 4,4-di-(t-butylperoxy)pentanohydrazide (I-1), 46.7 g (0.15 mole) of 98.4% ethyl 4,4-di-(t-butylperoxy)pentanoate and 90 g (about 1.50 moles) of 54% aqueous hydrazine in 325 mL of IPA were reacted at 25° C. for about 60 hours. Following the same procedure as described above, 37.4 g (85.4% of theory, uncorrected) of a white solid, mp, 79°-80° C. was obtained. The product had a neutralization equivalent of 294.4 (theory, 292.3) and an active oxygen content of 11.02% (theory, 10.95%). Hence, the assay of the product was 100% and the corrected yield was 85.4%. These product data confirm that the product was 4,4-di-(t-butylperoxy)pentanohydrazide (I-1).

EXAMPLE 2

Preparation of 4,4-Di-(t-amylperoxy) pentanohyrazide (I-2)

4,4-Di-(t-amylperoxy)pentanohydrazide was prepared by reacting ethyl 4,4-di-(t-amylperoxy)pentanoate with 9 molar excess of 54% aqueous hydrazine in a manner similar to that employed in Example 1 for the preparation of 4,4-di-(t-butylperoxy)pentanohydrazide. The product, 4,4-di-(t-amylperoxy)pentanohydrazide (I-2), had a DSC peroxide decomposition temperature of 171° C. The yield was 91%.

EXAMPLE 3

Preparation of 3,3-Di-(t-butylperoxy)butanohydrazide (I-3)

3,3-Di-(t-butylperoxy)butanohydrazide was prepared by reacting ethyl 3,3-di-(t-butylperoxy)butanoate with 9 molar excess of 54% aqueous hydrazine. A 3-neck flask equipped with a magnetic stirrer, a thermometer and an addition funnel was charged with 100 mL of IPA, 14.6 g (0.05 mole) of 100% ethyl 3,3-di-(t-butylperoxy)butanoate and 30 g (about 0.50 mole) of 54% aqueous hydrazine at 25° C. The solution was stirred for about 20 hours at 20°-22° C., then the reaction mass was poured into 1000 mL of water and extracted twice with 200 mL portions of methylene chloride. After drying over 10% by weight of anhydrous magnesium sulfate and separation of the spent desiccant by filtration, the methylene chloride was removed in vacuo leaving 14.3 g (>100% of theory, uncorrected) of a liquid product. 75 mL of pentane was added, the solution cooled to 0° C. and a solid precipitated. The solid was separated by filtration and air dried, leaving 4.8 g (35% of theory, uncorrected) of a white solid, mp, 62°-63° C.

A second preparation of I-3 was carried out in which methyl 3,3-di-(t-butylperoxy)butanoate (instead of ethyl 3,3-di-[t-butylperoxy]butanoate) was reacted with 9 molar excess of 54% aqueous hydrazine using a procedure similar to the above. A solid product (mp, 61°-62° C.) was obtained in an uncorrected yield of 81%. Hence, it appears that the methyl ester reacts more readily and completely with hydrazine than does the ethyl ester. The IR spectra of the two isolated solid products were identical. A DSC scan run on the latter prepared product showed a peroxide decomposition exotherm at 176° C. These product data indicate that the products obtained were the same composition, 3,3-di-(t-butylperoxy)butanohydrazide (I-3).

EXAMPLE 4

Preparation of 3-(1,4,4,6-Tetramethyl-2,3,7-trioxacycloheptyl)propionhydrazide (I-4)

3-(1,4,4,6-Tetramethyl-2,3,7-trioxacycloheptyl)propionhydrazide was prepared by reacting 3-(ethoxycarbonylethyl)-3,5,7,7-tetramethyl-1,2,4-trioxacycloheptane with 9 molar excess of 54% aqueous hydrazine. 3-(Ethoxycarbonylethyl)-3,5,7,7-tetramethyl-1,2,4-trioxacycloheptane was initially prepared in an assay of 89% and a corrected yield of 88% by reacting ethyl levulinate with 10% molar excess of 3-hydroxy-1,1-dimethylbutyl hydroperoxide using 70% aqueous sulfuric acid as a catalyst/dehydrating agent.

In the synthesis of the I-4, a 3-neck flask equipped with a magnetic stirrer, a thermometer and an addition funnel was charged with 125 mL of ethanol, 14.5 g (0.05 mole) of 89% 3-(ethoxycarbonylethyl)-3,5,7,7-tetramethyl-1,2,4-trioxayloheptane and 29.6 g (about 0.50 mole) of 54% aqueous hydrazine at 25° C. The solution was stirred for about 20 hours at 20°-25° C. Then the reaction mass was poured into 300 mL of water containing 0.45 mole of HCl . The pH was adjusted to 7 by addition of granular sodium carbonate. The solution was extracted twice with 200 mL portions of methylene chloride and the methylene chloride extractions were combined. After drying over 10% by weight of anhydrous magnesium sulfate and separation of the spent desiccant by filtration, the methylene chloride was removed in vacuo leaving 8.5 g (69% of theory, uncorrected) of a heavy yellow oil. 25 mL of pentane was added to the liquid product, and after stirring for 5 minutes at 25° C. the pentane was decanted off and residual pentane in the product layer was removed in vacuo leaving 6.6 g (54% of theory, uncorrected) of a heavy yellow oil. An IR spectrum of the product showed a broad carbonyl absorption band centered at 1660 cm$^{-1}$ and a broad NH band at 3300 cm$^{-1}$. Also present were small —OO— bands at 880 cm$^{-1}$, 860 cm$^{-1}$ and 840 cm$^{-1}$. A DSC scan of the product showed a peroxide decomposition exotherm at 229° C. These product data confirm that the product was 3-(1,4,4,6-tetramethyl-2,3,7-trioxacycloheptyl)propionhydrazide I-4.

EXAMPLE 5

Preparation of 1,3-Dimethyl-3-(t-butylperoxy)butyl Carbazate (I-5)

1,3-Dimethyl-3-(t-butylperoxy)butyl carbazate was prepared by reacting 1,3-dimethyl-3-(t-butylperoxy)butyl chloroformate with 11 molar excess of 54% aqueous hydrazine.

A jacketed glass reactor equipped with a mechanical stirrer, a thermometer and an addition funnel was charged with 100 mL of methylene chloride and 35.6 g (about 0.60 mole) of 54% aqueous hydrazine at 25° C. The resulting solution was cooled to 0° C. and was vigorously stirred while 13.3 g (0.05 mole) of 95% 1,3-dimethyl-3-(t-butylperoxy)butyl chloroformate was slowly added over a period of 20 minutes to the stirred solution. The resulting solution was further stirred at 0° C. for 90 minutes, then the solution was poured into 500 mL of water. About 35 mL of concentrated aqueous HCl was added to the resulting mixture in order to bring the pH to 7–8. Sodium hydrogen carbonate was added to buffer the mixture at a pH of 8. The methylene chloride layer was separated and washed once with 100 mL of water, then dried over 10% by weight of anhydrous magnesium sulfate. After separation of the spent desiccant by filtration, the methylene chloride was removed in vacuo leaving 14.3 g (>100% of theory, uncorrected) of liquid product. High performance liquid chromatography indicated that the purity of the product was about 85–90%. An IR spectrum of the product showed a strong carbonyl absorption band in the region 1710–1720 cm$^{-1}$ and a strong NH band at 3350 cm$^{-1}$. A DSC scan of the product showed a peroxide decomposition exotherm at 192° C. These product data and the method of synthesis confirm that the product was 1,3-dimethyl-3-(t-butylperoxy)butyl carbazate I-5.

EXAMPLE 6

Preparation of O-(1,3-Dimethyl-3-[t-butylperoxy]butyl) N-(2-Aminoethyl) Carbamate (I-6)

O-(1,3-Dimethyl-3-[t-butylperoxy]butyl) N-(2-aminoethyl) carbamate was prepared by reacting 1,3-dimethyl-3-(t-butylperoxy)butyl chloroformate with 4 molar excess of ethylenediamine.

A jacketed glass reactor equipped with a mechanical stirrer, a thermometer and an addition funnel was charged with 100 mL of methylene chloride and 15.0 g (0.25 mole) of ethylenediamine at 25° C. The resulting solution was vigorously stirred while 13.7 g (0.05 mole) of 92.2% 1,3-dimethyl-3-(t-butylperoxy)butyl chloroformate was slowly added over a period of 30 minutes to the stirred solution. The resulting solution became cloudy and was further stirred at 25° C. for 30 minutes, then 100 mL of 5% aqueous sodium hydroxide (0.125 mole) was added, the mixture stirred 5 minutes, then settled. The aqueous phase was discarded and the methylene chloride solution was washed five (5) times with 100 mL portions of water at 20°–25° C. in order to remove any excess ethylenediamine. The resulting methylene chloride solution was treated with 100 mL of 0.6N hydrochloric acid solution, the aqueous phase separated and washed once with 50 mL of methylene chloride. The aqueous phase was then treated with 100 mL of 1.0N sodium hydroxide solution and the resulting mixture was extracted twice with 75 mL portions of methylene chloride. The combined methylene chloride extracts were then washed three (3) times with 100 mL portions of water, then dried over 10% by weight of anhydrous magnesium sulfate. After separation of the spent desiccant by filtration, the methylene chloride was removed in vacuo leaving 11.2 g (81.2% of theory, uncorrected) of a colorless liquid product.

The product was found to have a neutralization equivalence of 277.3 compared to a theoretical neutralization equivalence of 276.3, therefore, the purity of the product appeared to be quite high. An IR spectrum of the product showed a strong carbonyl absorption band in the region about 1700 cm$^{-1}$, a strong NH band at 3180 cm$^{-1}$ and an —OO— absorption band at about 875 cm$^{-1}$. These product data and the method of synthesis confirm that the product was O-(1,3-dimethyl-3-[t-butylperoxy]butyl) N-(2-aminoethyl) carbamate I-6.

EXAMPLE 7

Preparation of 1-(2-Cyano-3,3-diphenylpropenoyl)-2-(4,4-di-[t-amylperoxy]pentanoyl)hydrazine (I-7)

2-Cyano-3,3-diphenylpropenoyl chloride was initially prepared by reacting 2-cyano-2,2-diphenylpropenoic acid with excess phosgene in the presence of N,N-dimethylformamide catalyst at about 40° C. Using a procedure similar to that employed for preparing I-6, 1-(2-cyano-3,3-diphenylpropenoyl)-2-(4,4-di-[t-amylperoxy]pentanoyl)hydrazine, I-7, was prepared by reacting 3.2 g (0.01 mole) of 4,4-di-(t-amylperoxy)pentanohydrazide with 2.7 g (0.01 mole) of 100% 2-cyano-3,3-diphenylpropenoyl chloride in the presence of 2.0 g (0.026 mole) of pyridine and 120 mL of methylene chloride. The reaction mixture was maintained at 0° C. over a period of about 75 minutes and then warmed to room temperature over a period of 60 minutes. Following a procedure similar to that employed in Example 6, 2.7 g (49% of theory, uncorrected) of light yellow solid having a melting point of 145°–148° C. (gassing) was obtained. An IR spectrum of the product showed an NH band centered at about 3190 cm$^{-1}$, hydrazide carbonyl bands at 1690 cm$^{-1}$ and 1640 cm$^{-1}$ and an —OO— band at about 860 cm$^{-1}$. A DSC scan of the product showed a peroxide decomposition exotherm at 175° C. These IR spectral and DSC product data, as well as the method of preparation, confirm that the product was the desired 1-(2-cyano-3,3-diphenylpropenoyl)-2-(4,4-di-[t-amylperoxy]pentanoyl)hydrazine, I-7.

EXAMPLE 8

Preparation of (2,2,6,6-Tetramethyl-4-piperidinyl)-(4,4-di-[t-butylperoxy]pentanoyl)hydrazone (I-8)

A 100 mL Erlenmeyer flask equipped with an air condenser and a magnetic stirring bar was charged with 2.9 g (0.01 mole) of 4,4-di-(t-butylperoxy)pentanohydrazide, 60 mL of methanol, 4.0 g (0.049 mole) of sodium acetate and 2.3 g (0.012 mole) of 2,2,6,6-tetramethyl-4-piperidone hydrochloride. The resulting mixture was then placed in a heated oil bath, magnetically stirred and refluxed (at about 76° C.) for 4 hours. The mixture was cooled to room temperature over about 16 hours. The mixture was then poured into about 300 mL of ice water and vigorously stirred. The aqueous solution was extracted twice with 100 mL portions of methylene chloride. The combined methylene chloride extracts were dried over 10% by weight of anhydrous magnesium sulfate. After separation of the spent desiccant by filtration, the methylene chloride was removed in vacuo leaving 4.2 g (89% of theory, uncorrected) of a paste. The paste was slurried with about 20 mL of pentane and the undissolved solid separated by filtration and air dried, leaving 1.3 g (28% of theory, uncorrected) of white solid, mp, 130°–135° C. An IR spectrum of the product showed two NH bands at about 3260 cm$^{-1}$ and 3190 cm$^{-1}$, carbonyl bands at 1690 cm$^{-1}$, 1660 cm$^{-1}$ and 1640 cm$^{-1}$ and an —OO— band at about 870 cm$^{-1}$. A DSC scan of the product showed a peroxide decomposition exotherm at 177° C. These IR spectral and DSC product data, as well as the method of preparation, confirm that the product was the desired (2,2,6,6-tetramethyl-4-piperidinyl)-4,4-di-[t-butylperoxy]pentanoyl)hydrazone, I-8.

EXAMPLE 9

Preparation of
1-Benzoyl-2-(4,4-di-[t-butylperoxy]pentanoyl)hydrazine (t-9)

Using a procedure similar to that employed for preparing I-7, 1-benzoyl-2-(4,4-di-[t-butylperoxy]-pentanoyl)hydrazine was prepared by reacting 2.9 g (0.01 mole) of 4,4-di-(t-butylperoxy)pentanohydrazide with 1.6 g (0.011 mole) of 100% benzoyl chloride in the presence of 2.0 g (0.026 mole) of pyridine and 100 mL of methylene chloride at 20° C. Following a procedure similar to that employed in Example 7, 2.6 g (65% of theory, uncorrected) of a white solid having a melting point of 147°–149° C. was obtained. An IR spectrum of the product showed an NH band centered at about 3230 cm$^{-1}$ a hydrazide carbonyl band at 1620 cm$^{-1}$ and an —OO— band at about 880 cm$^{-1}$. A DSC scan of the product showed a peroxide decomposition exotherm at 177° C. These IR spectral and DSC product data, as well as the method of preparation, confirm that the product was the desired 1-benzoyl-2-(4,4-di-[t-butylperoxy]pentanoyl)hydrazine, I-9.

EXAMPLE 10

1-(2-Ethylhexoxycarbonyl)-2-(4,4-di-[t-butylperoxy]-pentanoyl)hydrazine (t-10)

Using a procedure similar to that employed for preparing I 7, 1-(2-ethylhexoxycarbonyl)-2-(4,4-di-[t-butylperoxy]pentanoyl)hydrazine was prepared by reacting 2.9 g (0.01 mole) of 4,4-di-(t-butylperoxy)pentanohydrazide with 2.0 g (0.01 mole) of 99% 2-ethylhexyl chloroformate in the presence of 2.0 g (0.026 mole) of pyridine and 100 mL of methylene chloride at 20° C. Following a procedure similar to that employed in Example 7, 4.6 g (>100% of theory, uncorrected) of a yellow liquid product was obtained. An IR spectrum of the product showed an NH band centered at about 3250 cm$^{-1}$, carbonyl bands at 1720 cm$^{-1}$ and 1670 cm$^{-1}$ and an —OO— band at about 870 cm$^{-1}$. A DSC scan of the product showed a peroxide decomposition exotherm at 176° C. These IR spectral and DSC product data, as well as the method of preparation, confirm that the product was the desired 1-(2-ethylhexoxycarbonyl)-2-(4,4-di-[t-butylperoxy]pentanoyl)hydrazine, I-10.

EXAMPLE 11

Preparation of 3-Oxapentane-1,5-diyl
Bis(2-[4,4-di-(t-butylperoxy) pentanoyl]carbazate)
(I-11)

Using a procedure similar to that employed for preparing of the title compound of I-7, 3-oxapentane-1,5-diyl bis(2-[4,4-di-(t-butylperoxy)pentanoyl]carbazate) was prepared by reacting 2.9 g (0.01 mole) of 4,4-di-(t-butylperoxy)pentanohydrazide with 1.16 g (0.005 mole) of 99+% diethylene glycol bis(chloroformate) in the presence of 2.0 g (0.026 mole) of pyridine and 100 mL of methylene chloride at 20° C. Following a procedure similar to that employed in Example 7, 3.7 g (100% of theory, uncorrected) of a white solid having a melting point of about 45°–50° C. was obtained. An IR spectrum of the product showed an NH band centered at about 3250 cm$^{-1}$, carbonyl bands at 1730 cm$^{-1}$ and 1670 cm$^{-1}$ and an —OO— band at about 870 cm$^{-1}$. A DSC scan of the product showed a peroxide decomposition exotherm at 175° C. These IR spectral and DSC product data, as well as the method of preparation, confirm that the product was the desired 3-oxapentane-1,5-diyl bis(2-[4,4-di-(t-butylperoxy)pentanoyl]carbazate), I-11.

EXAMPLE 12

Preparation of 2,2′-Di-(3,3-di-[t-butylperoxy]butanoyl)
Dodecanedioic Acid Dihydrazide (I-12)

Using a procedure similar to that employed for preparing I-7, 2,2′-di-(3,3-di-[t-butylperoxy]butanoyl) dodecanedioic acid dihydrazide was prepared by reacting 2.8 g (0.01 mole) of 3,3-di-(t-butylperoxy)butanohydrazide with 1.44 g (0.005 mole) of 92.6% 1,12-dodecanedioyl dichloride in the presence of 2.0 g (0.026 mole) of pyridine and 100 mL of methylene chloride at 20° C. Following a procedure similar to that employed in Example 7, 3.5 g (92% of theory, uncorrected) of a white solid having a melting point of 113°–116° C. was obtained. An IR spectrum of the product showed an NH band centered at about 3200 cm$^{-1}$, a carbonyl band at about 1610–1620 cm$^{-1}$ and an —OO— band at about 875 cm$^{-1}$. A DSC scan of the product showed a peroxide decomposition exotherm at 181° C. These IR spectral and DSC product data, as well as the method of preparation, confirm that the product was the desired 2,2′-di-(3,3-di-[t-butylperoxy]butanoyl) dodecanedioic acid dihydrazide, I-12.

EXAMPLE 13

Preparation of N′-(3-Carboxypropionyl)
O-(1,3-Dimethyl-3-[t-butylperoxy]-butyl) Carbazate
(I-13)

N′-(3-Carboxypropionyl) O-(1,3-dimethyl-3-[t-butylperoxy]butyl) carbazate was prepared by reacting 6.9 g (0.025 mole) of 1,3-dimethyl-3-(t-butylperoxy)butyl carbazate with 2.6 g (0.026 mole) of about 100% succinic anhydride in the presence of 100 mL of methylene chloride at 25° C. Initially, both reactants went into solution. After about 5 minutes, a solid started to precipitate from the solution and there was a 1°–2° C. rise in temperature. The mixture was further stirred for 60 minutes at 25° C. after which the solid was separated by filtration, washed with methylene chloride and dried. 7.3 g (84% of theory, uncorrected) of a white solid having a melting point of 141°–143° C. was obtained. An IR spectrum of the product showed two NH bands at 3250 cm$^{-1}$ and 3100 cm$^{-1}$, a carbazate carbonyl band at about 1720 cm$^{-1}$, a broad carbonyl band at 1680 cm$^{-1}$ and an —OO— band at about 870 cm$^{-1}$. A DSC scan of the product showed a peroxide decomposition exotherm at 197° C. These IR spectral and DSC product data, as well as the method of preparation, confirm that the product was the desired N′-(3-carboxypropionly) O-(1,3-dimethyl-3-[t-butylperoxy]butyl) carbazate, I13.

EXAMPLE 14

Preparation of 3-(1,4,4,6-Tetramethyl-2,3,7-trioxacycloheptyl)-N'-(3-carboxypropionyl)propionhydrazide (I-14)

3-(1,4,4,6-Tetramethyl-2,3,7-trioxacycloheptyl)-N'-(3-carboxypropionyl)propionhydrazide was prepared by reacting 1.2 g (0.0044 mole) of 3-(1,4,4,6-tetramethyl-2,3,7-trioxacycloheptyl)propionhydrazide with 0.5 g (0.0050 mole) of about 100% succinic anhydride in the presence of 30 mL of methylene chloride at 25° C. Initially, both reactants went into solution and no precipitation occurred during 120 minutes at 25° C. Then 100 mL of pentane was added to the solution and a solid began to precipitate. The mixture was stirred for an additional 30 minutes at 25° C., then the solid was separated by filtration, washed with pentane and dried. 1.2 g (80% of theory, uncorrected) of a white solid having a melting point of 122°-126° C. was obtained. An IR spectrum of the product showed two NH bands at 3240 cm$^{-1}$ and 3100 cm$^{-1}$, a hydrazide carbonyl band at about 1706 cm$^{-1}$, an acid carbonyl band at 1675 cm$^{-1}$ and a small —OO— band at about 900 cm$^{-1}$. A DSC scan of the product showed a peroxide decomposition exotherm at 226° C. These IR spectral and DSC product data, as well as the method of preparation, confirm that the product was the desired 3-(1,4,4,6-tetramethyl-2,3,7-trioxacycloheptyl)-N'-(3-carboxypropionyl)propionhydrazide, I-14.

EXAMPLE 15

Preparation of a Polymeric Peroxide (I-15) via Reaction of 1,3-Dimethyl-3-(t-butylperoxy)butyl Carbazate (I-5) with a Poly(styrene-co-maleic anhydride) Copolymer In this example, a poly(styrene-co-maleic anhydride) copolymer, Dylark TM 232 (Arco), containing about 9% by weight of maleic anhydride (MA) units, was reacted with 1,3-dimethyl-3-(t-butylperoxy)butyl carbazate (I-5) to form a poly(styrene-co-maleamic acid) copolymer possessing pendant peroxide groups.

A 125 mL Erlenmeyer flask equipped with a magnetic stirring bar was charged with 10 g of Dylark TM 232 poly(styrene-co-maleic anhydride) copolymer (0.0092 mole of MA units) and 50 g of toluene and the mixture was stirred and heated to 80°-90° C. in order to dissolve the polymer. Then 2.1 g (0.0076 mole) of 1,3-dimethyl-3-(t-butyl-peroxy)butyl carbazate (I-5) in 20 g of toluene was rapidly added to the toluene solution of Dylark TM 232 and the resulting solution was allowed to cool from 85° C. to 35° C. over a period of 150 minutes. The solution was then added to 500 mL of vigorously stirred methanol in a stainless steel Waring blender in order to precipitate the polymer. The solid polymer was washed twice at room temperature with 500 mL portions of vigorously stirred methanol in the Waring blender in order to remove unreacted I-5 and other impurities from the polymer. The polymer was then dried. 10.7 g (theoretical yield =11.9 g; 90% of theory, uncorrected) of white granular polymer was obtained. A DSC scan of the product showed a peroxide decomposition exotherm at 208° C. It should be noted that I-5 had a peroxide decomposition temperature of 197° C. (see Example 5). Based on the DSC data, the method of preparation and the method of isolation, the polymeric product produced in this example is confirmed as being a poly(styrene-co-maleamic acid) copolymer possessing pendant peroxide groups. Furthermore, the pendant peroxide groups have the 1,3-dimethyl-3-(t-butylperoxy)butyl carbazate (I-5) structure. Thus, I-15 was produced.

EXAMPLE 16

Preparation of a Polymeric Peroxide (I-16) via Reaction of 3,3-Di-(t-butylperoxy)butanohydrazide (I-3) with a Poly(1-octadecene-co-maleic anhydride) Copolymer In this example, a poly(1-octadecene-co-maleic anhydride) alternating copolymer, PA-18 TM (Gulf), containing about 29% by weight of MA units, was reacted with 3,3-di-(t-butylperoxy)butanohydrazide (I-3) to form a poly(1-octadecene-co-maleamic acid) copolymer possessing pendant peroxide groups.

A 50 mL Erlenmeyer flask equipped with a magnetic stirring bar was charged with 1.00 g of Gulf's PA-18 TM poly(1-octadecene-co-maleic anhydride) alternating copolymer (0.0029 mole of MA units), 0.56 g (0.0020 mole) of 3,3-di-(t-butylperoxy)butanohydrazide (I-3) and 10 g of toluene. The mixture was stirred and heated at 50° C. for 30 minutes. An IR spectrum of the solution showed that the anhydride absorption bands at 1770 cm$^{-1}$ and at 1850 cm$^{-1}$ for the starting PA-18 copolymer were significantly diminished as was the NH band at about 3300 cm$^{-1}$ for the starting hydrazine (I-3). The strong amide carbonyl band at 1640 cm$^{-1}$ for the starting hydrazine (I-3) was also gone. A new, strong amic acid carbonyl band at 1700 cm$^{-1}$ was observed for the product solution. Based on the IR data and method of preparation the polymeric product produced in this example is confirmed as being a poly(1-octadecene-co-maleamic acid) copolymer possessing pendant peroxide groups. Furthermore, the pendant peroxide groups have the 3,3-di-(t-butylperoxy)-butanohydrazide (I-3) structure. Thus, the I-16 copolymer was produced.

EXAMPLE 17

Preparation of a Polymeric Peroxide (I-17) via Reaction of 0-(1,3-Dimethyl-3-[t-butylperoxy]butyl) N-(2-Aminoethyl) Carbamate (I-6) with a Poly(1-octadecene-co-maleic anhydride) Copolymer In this example a poly(1-octadecene-co-maleic anhydride) alternating copolymer, PA-18 TM (Gulf), containing about 29% by weight of MA units, was reacted with O-(1,3-dimethyl-3-[t-butylperoxy]butyl) N-(2-aminoethyl) carbamate (I-6) to form a poly(1-octadecene-co-maleamic acid) copolymer possessing pendant peroxide groups.

A 125 mL Erlenmeyer flask equipped with a magnetic stirring bar was charged with 28.0 g of a toluene solution containing 7.0 g of Gulf's PA-18 poly(1-octadecene-co-maleic anhydride) alternating copolymer (0.0200 mole of MA units) and 4.6 g (0.0166 mole) of O-(1,3-dimethyl-3-[t-butylperoxy]butyl) N-(2-aminoethyl) carbamate (I-6) at room temperature. The mixture was stirred and heated to and held at 55° C. for 300 minutes. An IR spectrum of the PA-18 solution showed anhydride carbonyl absorption bands at 1775 cm$^{-1}$ and at 1855 cm$^{-1}$ and a 5-membered cyclic anhydride stretching absorption band at about 925 cm$^{-1}$. An IR spectrum of the product solution showed that the anhydride absorption bands at 1775 cm$^{-1}$ and at 1855 cm$^{-1}$ were significantly diminished. In addition, the 5-membered cyclic anhydride stretching absorption band at about 925 cm$^{-1}$ was nearly gone in the product solution. Furthermore, an amide carbonyl band was present at about 1700 cm$^{-1}$ and an —OO— band was present at about 870 cm$^{-1}$ in the product solution. The product solution became extremely viscous which was consistent with the formation of a poly(amic acid) solution (owing to formation of a hydrogen bond network). Based on the IR data, the method of preparation and the solution properties, the polymeric product produced in this example is confirmed as being a poly(1-octadecene-co-maleamic acid) copolymer possessing pendant peroxide groups. Furthermore, the pendant peroxide groups have the O-(1,3-dimethyl-3-[t-butylperoxy]butyl) N-(2-aminoethyl) carbamate (I-6) structure. Thus, the I-17 copolymer was produced.

EXAMPLE 18

138° C. SPI Exotherms of 4,4-Di-t-butylperoxy)pentanohydrazide (I-1)

The unsaturated polyester resin composition employed in this example was a mixture of an unsaturated polyester and styrene monomer. The unsaturated polyester was an alkyd resin made by esterifying the following components:

| Component (moles) | Quantity |
|---|---|
| Maleic Anhydride | 1.0 |
| Phthalic Anhydride | 1.0 |
| Propylene Glycol | 2.2 |

0.013% by weight of hydroquinone inhibitor was added to the resulting resin. The alkyd resin had an Acid No. of 45–50. Seven (7) parts by weight of the above unsaturated polyester alkyd were diluted with three (3) parts by weight of monomeric styrene. The resulting unsaturated polyester resin composition had the following properties:
  a. Viscosity (Brookfield No. 2 at 20 r.p.m.): 13.0 poise
  b. Specific gravity: 1.14

Gelation and cure characteristics of ethyl 3,3-di-(t-butylperoxy)butanoate (A-1), a well known curing catalyst for unsaturated polyester resin compositions, and 4,4-di-(t-butylperoxy)pentanohydrazide (I-1), a composition of the present invention, were determined using the Standard SPI Exotherm Procedure ("SPI Procedure for Running Exotherm Curves-Polyester Resins," published in the Preprint of the 16th Annual Conference-Reinforced Plastics Division, Society of the Plastics Industry, Inc., February, 1961). Using the procedure at 138° C. (280° F.), A-1 and I-1 were evaluated.

The results are summarized in Table 18-1 and show that I-1, a composition of the present invention, is surprisingly active in gelling and curing the unsaturated polyester resin. This is a surprising result in that the hydrazino group of I-1 would be expected to react with free radicals and adversely affect the curing. The use of I-1 with its hydrazino functionality not only did not adversely affect the cure, it enhanced the cure as indicated by the substantially faster curing time.

TABLE 18-1

| SPI Exotherm Data at 138° C. | | | | | |
|---|---|---|---|---|---|
| Curing Catalyst | Level, % | Gel, mins | Cure, mins | Peak Exotherm, °F. | Barcol Hardness |
| A-1 | 1.0 | 2.2 | 2.8 | 445 | 45–50 |
| I-1 | 1.0 | 1.0 | 2.2 | 400 | 45–50 |

EXAMPLE 19

Preparation of 1,3-Dimethyl-3-(2-ethylhexanoylperoxy)butyl Carbazate (I-19)

1,3-Dimethyl-3-(2-ethylhexanoylperoxy)butyl carbazate was prepared by reacting 1,3-dimethyl-3-(2-ethylhexanoylperoxy)butyl chloroformate with 11 molar excess of 54% aqueous hydrazine. 1,3-Dimethyl-3-(2-ethyl-hexanoylperoxy)butyl chloroformate was initially prepared with a purity of 72% by reacting 3-hydroxy-1,1-dimethylbutyl peroxy-2-ethylhexanoate with excess phosgene followed by removal of excess phosgene.

A jacketed glass reactor equipped with a mechanical stirrer, a thermometer and an addition funnel was charged with 80 mL of methylene chloride and 23.1 g (about 0.39 mole) of 54% aqueous hydrazine at 25° C. The resulting solution was cooled to 0° C. and was vigorously stirred while 15.7 g (0.035 mole) of 72% 1,3-dimethyl-3-(2-ethylhexanoylperoxy)butyl chloroformate in 20 mL of methylene chloride was slowly added over a period of 20 minutes to the stirred solution at 0°–5° C. The resulting solution was further stirred at 0°–5° C. for 120 minutes. The resulting solution was then washed six times with 50 mL portions of water and the methylene chloride solution was dried over 10% by weight of anhydrous magnesium sulfate. After separation of the spent desiccant by filtration, the methylene chloride was removed in vacuo leaving 11.3 g (>100% of theory, uncorrected) of yellow liquid product. An IR spectrum of the product showed strong carbonyl absorption bands at 1770 cm$^{-1}$, 1720 cm$^{-1}$ and 1650 cm$^{-1}$ (amide carbonyl) and a strong NH band at 3350 cm$^{-1}$. A DSC scan of the product showed a peroxide decomposition exotherm at 130° C. These product data and the method of synthesis confirm that the product was 1,3-dimethyl-3-(2-ethylhexanoylperoxy)butyl carbazate, I-19.

EXAMPLE 20

Preparation of O-(1,3-Dimethyl-3-[2-ethylhexanoylperoxy]butyl) N'-(1,3-Dimethyl-3-[t-butylperoxy]-butoxycarbonyl) Carbazate (I-20)

Preparation of O-(1,3-dimethyl-3-[2-ethylhexanoylperoxy]butyl) N'-(1,3-dimethyl-3-[t-butylperoxy]butoxycarbonyl) carbazate, a sequential peroxide, was prepared by reacting equal molar amounts of 1,3-dimethyl-3-(2-ethylhexanoylperoxy)butyl chloroformate and 1,3-dimethyl-3-(t-butylperoxy)butyl carbazate (I-5) in the presence of excess pyridine.

A three-neck flask equipped with a magnetic stirring bar, a thermometer, a condenser and an addition funnel was charged with 80 mL of methylene chloride, 2.0 g (0.026 mole) of pyridine and 2.7 g (0.010 mole) of 1,3-dimethyl-3-(t-butylperoxy)butyl carbazate (I-5). This solution was stirred at 20°–25° C. and a solution of 4.5 g (0.010 mole) of 72% 1,3-dimethyl-3-(2-ethylhexanoylperoxy)butyl chloroformate in 20 mL of methylene chloride was slowly added to it. A very slight exotherm was noted. The reaction mixture was stirred for 4 hours at 25° C. after which it was washed with two 25 mL portions of 5% aqueous sulfuric acid solution, followed by three 50 mL water washes. The methylene chloride solution was then dried over 10% by weight of anhydrous magnesium sulfate. After separation of the spent desiccant by filtration, the methylene chloride was removed in vacuo leaving 5.1 g (96% of theory, uncorrected) of a straw-colored liquid product. An IR spectrum of the product showed a strong carbonyl absorption band at 1730 cm$^{-1}$ and a strong NH band at 3360 cm$^{-1}$. A DSC scan of the product showed, as expected, two peroxide decomposition exotherms, one at about 125° C. and the other at about 185° C. These product data and the method of synthesis confirm that the product was O-(1,3-dimethyl-3-[2-ethylhexanoylperoxy]butyl) N'-(1,3-dimethyl-3-[t-butylperoxy]butoxycarbonyl) carbazate, I-20.

EXAMPLE 21

Preparation of
O-(1,3-Dimethyl-3-[t-butylperoxy]butyl)N-Succinimido Carbamate (I-21)

O-(1,3-Dimethyl-3-[t-butylperoxy]butyl) N-succinimido carbamate was prepared by reacting N'-(3-carboxypropionyl) 1,3-dimethyl-3-(t-butylperoxy)butyl carbazate (I-13) with acetic anhydride and sodium acetate.

A 3-neck flask equipped with a magnetic stirrer, a thermometer and a reflux condenser was charged with 7.0 g (0.020 mole) of N'-(3-carboxypropionyl) 1,3-dimethyl-3-(t-butylperoxy)butyl carbazate (I-13, 100% assay assumed), 1.3 g (0.016 mole) of sodium acetate and 20.4 g (0.200 mole) of acetic anhydride at room temperature. The reaction mass was stirred, heated to and held at 75° C. for 10–15 minutes. The starting peroxide went into solution. The reaction mass was then cooled to room temperature, then poured into 200 mL of water, stirred for 30 minutes at room temperature and extracted twice with 75 mL portions of methylene chloride. The combined methylene chloride extracts were then washed at room temperature twice with 100 mL portions of water, then twice with 80 mL portions of 8% aqueous NaHCO$_3$ solution. The methylene chloride solution was then dried over 10% by weight of anhydrous magnesium sulfate. After separation of the spent desiccant by filtration, the methylene chloride was removed in vacuo, leaving 6.7 g (100% of theory, uncorrected) of a viscous colorless liquid product. The product was then dissolved in pentane and over a period of several hours a solid precipitated from solution. The white solid was separated by filtration, washed with fresh pentane and dried. 2.5 g (38% of theory, uncorrected) of a white solid having a melting point of 79°–83° C. was obtained. An IR spectrum of the product showed an NH band (sharp) at 3300 cm$^{-1}$, a small imide carbonyl band at 1790 cm$^{-1}$, a strong imide carbonyl band at 1720 cm$^{-1}$ and a small —OO— band at about 875 cm$^{-1}$. A DSC scan of the product showed a peroxide decomposition exotherm at about 195° C. IR spectral and DSC data and the method of synthesis confirm that the product was O-(1,3-dimethyl-3-[t-butylperoxy]butyl) N-succinimido carbamate, I-21, the desired product.

EXAMPLE 22

Preparation of O-(1,3-Dimethyl-3-[t-butylperoxy]butyl) N-Maleimido Carbamate (I-22)

O-(1,3-Dimethyl-3-[t-butylperoxy]butyl) N-maleimido carbamate was prepared by reacting 1,3-dimethyl-3-(t-butylperoxy)butyl carbazate (I-5) with maleic anhydride to form the O-(1,3-dimethyl-3-[t-butylperoxy]butyl) N'-(cis-3-carboxypropenoyl) carbazate intermediate, followed by subsequent treatment with acetic anhydride and sodium acetate.

A 3-neck flask equipped with a magnetic stirrer, a thermometer and a reflux condenser was charged with 100 mL of methylene chloride, 2.5 g (0.026 mole) of maleic anhydride and 6.9 g (about 90% pure; 0.025 mole) of 1,3-dimethyl-3-(t-butylperoxy)butyl carbazate (I-5). The solution was stirred for 60 minutes at room temperature. No solid formed. The resulting solution was stripped of solvent, leaving 9.3 g of glassy product. This was assumed to be the maleamic acid intermediate, O-(1,3-dimethyl-3-[t-butylperoxy]butyl) N'-(cis-3-carboxypropenoyl) carbazate.

The intermediate was then treated with 25.5 g (0.250 mole) of acetic anhydride and 1.7 g (0.021 mole) of sodium acetate and transferred to a 3-neck flask equipped with a magnetic stirrer, a thermometer and a reflux condenser. The mixture was stirred, heated to and held at 70°–80° C. for 11 minutes. During the stir period at 70°–80° C., the intermediate became less viscous, indicating that the desired product was forming. The resulting reaction mixture was then poured into 300 mL of water, stirred for 30 minutes at room temperature and extracted twice with 75 mL portions of methylene chloride. The combined methylene chloride extracts were then washed twice at room temperature with 100 mL portions of water. The methylene chloride solution was then dried over 10% by weight of anhydrous magnesium sulfate. After separation of the spent desiccant by filtration, the methylene chloride was removed in vacuo leaving 9.3 g (>100% of theory, uncorrected) of a yellow, low viscosity liquid which had a strong odor.

The product was dissolved in 100 mL of methylene chloride and the methylene chloride solution was washed twice with 90 mL portions of 3% aqueous NaOH solution. The aqueous layers became yellow. The methylene chloride solution was then dried over 10% by weight of anhydrous magnesium sulfate, and, after separation of the spent desiccant by filtration, the methylene chloride was removed in vacuo, leaving 3.0 g (37% of theory, uncorrected) of a slushy solid. 30 mL of pentane was added and the white solid was separated by filtration, washed with fresh pentane and dried to give 1.4 g (17% of theory, uncorrected) of white solid having a melting point of 94°–97° C. An IR spectrum of the product showed an NH band at about 3360 cm$^{-1}$, a small imide carbonyl band at 1790 cm$^{-1}$, a strong imide carbonyl band at 1730 cm$^{-1}$ and a small —OO— band at about 865 cm$^{-1}$. Also present in the IR spectrum was a weak C=C band at about 1640 cm. A DSC scan of the product showed a peroxide decomposition exotherm at about 195° C. IR spectral and DSC data and the method of synthesis confirm that the product was O-(1,3-dimethyl-3-[t-butylperoxy]butyl) N-maleimido carbamate, I-22, the desired product.

EXAMPLE 23

Preparation of a Poly(1-octadecene-co-maleamic acid) Copolymer Possessing Pendant Peroxide Groups (I-23) via Reaction of 1,3-Dimethyl-3-(t-butylperoxy)butyl Carbazate (I-5) with a Poly(1-octadecene-co-maleic anhydride) Copolymer In this example a poly(1-octadecene-co-maleic anhydride) alternating copolymer, PA-18 ™ (Gulf), containing about 29% by weight of MA units, was reacted with 1,3-dimethyl-3-(t-butylperoxy)butyl carbazate (I-5) to form a poly(1-octadecene-co-maleamic acid) copolymer possessing pendant peroxide groups (I-23).

A 125 mL Erlenmeyer flask equipped with a magnetic stirring bar and a thermometer was charged with 28.0 g of a toluene solution containing 7.0 g of Gulf's PA-18 ™ poly(1-octadecene-co-maleic anhydride) alternating copolymer (0.020 mole of MA units) and 6.0 g (0.022 mole) of 1,3-dimethyl-3-(t-butylperoxy)butyl carbazate (I-5) at room temperature. The mixture was stirred, heated to and held at 95° C. for 240 minutes. An initial IR spectrum of the PA-18 ™ solution showed anhydride carbonyl absorption bands at 1780 cm$^{-1}$ and at 1855 cm$^{-1}$ and a 5-membered cyclic anhydride stretching absorption band at about 925 cm$^{-1}$. An IR spectrum of the product solution after 240 minutes at 95° C. showed that the anhydride absorption bands at 1780 cm$^{-1}$ and at 1855 cm$^{-1}$ were essentially gone. In addition, the 5-membered cyclic anhydride stretching absorption band at about 925 cm$^{-1}$ was nearly gone in the product solution. Furthermore, an amide carbonyl band was present at about 1720 cm$^{-1}$ and an —OO— band was present at about 870 cm$^{-1}$ in the product solution. The product solution became extremely viscous which was consistent with the formation of a poly(maleamic acid) solution (owing to formation of a hydrogen bond network).

The product solution was poured into a shallow glass bake pan and placed in a hood in order to volatilize the toluene. After three days, a brittle polymer film formed in the bottom of the bake pan. The film was broken up with a metal spatula, then the resulting polymer was washed three times with 100 mL portions of methanol in order to remove unreacted 1,3-dimethyl-3-(t-butylperoxy)butyl carbazate, I-5. (I-5 was found to be completely miscible with methanol.) The methanol-swollen polymer was then allowed to dry over a period of two days. The methanol extracts were combined and the methanol was allowed to evaporate over a period of two days at room temperature. About 0.5 g of a yellow liquid was obtained which was identified as 1,3-dimethyl-3-(t-butylperoxy)butyl carbazate, I-5. The dried polymer obtained after two days of drying was crushed to form 9.0 g (75% of theory, uncorrected) of light yellow powder. An IR spectrum of the resin product as a Nujol mull showed a carboxylic acid OH band at about 3500 cm$^{-1}$, an NH band at about 3280 cm$^{-1}$, an amide carbonyl band at about 1720 cm$^{-1}$ and an —OO— band at about 870 cm$^{-1}$. A DSC scan run on the product showed a peroxide decomposition exotherm at about 195° C.

Based on the IR data, the method of preparation, the DSC decomposition data and solution properties, the polymeric product produced in this example is confirmed as being a poly(1-octadecene-co-maleamic acid) copolymer possessing pendant peroxide groups, I-23. Furthermore, the pendant peroxide groups have the 1,3-dimethyl-3-(t-butylperoxy)butyl carbazate (I-5) structure.

EXAMPLE 24

Conversion of a Poly(1-octadecene-co-maleamic acid) Copolymer Possessing Pendant Peroxide Groups (I-23) to a Poly(1-octadecene-co-maleimide) Copolymer Possessing Pendant Peroxide Groups (I-24) via Reaction with Acetic Anhydride and Sodium Acetate.

In this example a poly(1-octadecene-co-maleamic acid) copolymer possessing pendant peroxide groups, I-23, was treated with acetic anhydride and sodium acetate to form the desired poly(1-octadecene-co-maleimide) copolymer possessing pendant peroxide groups, I-24.

A 3-neck flask equipped with a magnetic stirring bar and a thermometer was charged with 100 mL toluene, 8.0 g (13.37 mmoles of maleamic acid units) of poly(1-octadecene-co-maleamic acid) copolymer possessing pendant peroxide groups, I-23, 1.3 g (0.016 mole) of sodium acetate and 20.4 g (0.200 mole) of acetic anhydride. The resulting mixture was stirred, then heated to and held at 85°–95° C. for 60 minutes. The mixture was then cooled to room temperature and was subsequently washed four times with hot (45°–50° C.) water over periods of 10 minutes. The resulting toluene solution was then dried over 10% by weight of anhydrous magnesium sulfate, and, after separation of the spent desiccant by filtration, the product solution was poured into a shallow glass bake pan and placed in a hood in order to volatilize the toluene. After five days a sticky polymer film formed in the bottom of the bake pan. The resulting resin no longer had the odor of toluene.

The film was broken up with a metal spatula and 6.0 g (77% of theory, uncorrected) of rubbery resin were obtained. In addition, whereas the product resin was soluble in hexane, the starting resin, I-23, was not. A dry film of the product resin was cast onto an NaCl IR plate and an IR spectrum was obtained. A small NH band at about 330 cm$^{-1}$, and imide carbonyl band at about 1730 cm$^{-1}$ and an —OO— band at about 870 cm$^{-1}$ were observed. A dry film of starting poly(1-octadecene-co-maleamic acid) copolymer possessing pendant peroxide groups, I-23, was cast onto an NaCl IR plate from a toluene solution. An IR spectrum was observed that was significantly different than that of the product resin. Present were a broad carboxylic acid OH band at about 3500 cm$^{1}$, a broad and strong NH band at about 3290 cm$^{-1}$, a broad carbonyl band centered about 1720 cm$^{-1}$ with prominent shoulders at about 1850 cm$^{-1}$, 1780 cm$^{-1}$ and 1650 cm$^{-1}$, and an —OO— band at about 870 cm$^{-1}$. A DSC scan of the product resin showed a peroxide decomposition exotherm at 197° C.

Based on the IR data, the method of preparation, the DSC decomposition data and solution properties the polymeric product produced in this example is the desired poly(1-octadecene-co-maleimide) copolymer possessing pendant peroxide groups, I-24. Furthermore, the pendant peroxide groups have the 1,3-dimethyl-3-(t-butylperoxy)butyl carbazate (I-5) structure.

The present invention may be embodied in other specific forms without departing from the spirit or essential attributes thereof and, accordingly, reference should be made to the appended claims, rather than to the foregoing specification as indicating the scope of the invention.

I claim:

1. A process for preparing a block or graft copolymer by reacting, under conditions effective to form the block or graft copolymer, a polymer or monomer used to form the block or graft copolymer with a polymeric peroxide of Structure A1:

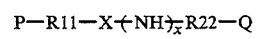

A1 where x is 0 or 1;

P is a peroxide-containing mono-radical having a structure:

$$R-OO-\underset{}{\overset{O}{\underset{\|}{C}}}-, \quad R1-\overset{O}{\underset{\|}{C}}-OO-\underset{R3}{\overset{R2}{\underset{|}{C}}}-,$$

$$R-OO-\overset{O}{\underset{\|}{C}}-O-, \quad R1'-O-\overset{O}{\underset{\|}{C}}-OO-\underset{R3}{\overset{R2}{\underset{|}{C}}}-,$$

$$R-OO-\underset{R3}{\overset{R2}{\underset{|}{C}}}-, \quad R-OO-\underset{OO---R}{\overset{R2}{\underset{|}{C}}}$$

$$(CH_2)_w \underset{\underset{R3}{C}\diagdown R4}{\overset{\overset{R3}{C}-OO}{\diagup}} \diagdown_{R2}^{C} ;$$

where w is 1 or 2;

R is a substituted or unsubstituted t-alkyl radical of 4 to 12 carbons, a substituted or unsubstituted t-aralkyl radical of 9 to 13 carbons, a t-cycloalkyl radical of 5 to 12 carbons or a substituted or unsubstituted t-alkynyl radical of 5 to 10 carbons;

R1 is a substituted or unsubstituted, branched or unbranched, alkyl radical of 1 to 13 carbons, a substituted or unsubstituted cycloalkyl radical of 5 to 10 carbons, a substituted or unsubstituted, branched or unbranched, aralkyl radical of 7 to 11 carbons or a substituted or unsubstituted aryl radical of 6 to 10 carbons;

R1' is a substituted or unsubstituted, branched or unbranched, alkyl radical of 1 to 13 carbons, a substituted or unsubstituted cycloalkyl radical of 5 to 10 carbons or a substituted or unsubstituted, branched or unbranched, aralkyl radical of 7 to 11 carbons;

R2 and R3 are the same or different and are substituted or unsubstituted alkyl radicals of 1 to 4 carbons;

the substituents for R, R1, R1', R2 and R3 being alkyl radicals of 1 to 4 carbons, chloro or bromo;

R4 is hydrogen, a substituted or unsubstituted alkyl radical of 1 to 10 carbons or a substituted or unsubstituted aryl radical of 6 to 10 carbons, the R4 substituents being one or more alkyl radicals of 1 to 8 carbons, chloro, bromo or carboxy;

T is nothing or —O—;

R11 is a substituted or unsubstituted alkylene diradical of 2 to 8 carbons or a substituted or unsubstituted 1, 2-, 1,3- or 1,4-phenylene diradical, the R11 substituents being alkyl radicals of 1 to 4 carbons, chloro or bromo;

X is nothing, $$-\overset{O}{\underset{\|}{C}}-, \quad -O-\overset{O}{\underset{\|}{C}}- \quad \text{or} \quad -C(R2)(R3)-;$$

R22 is nothing, a substituted or unsubstituted alkylene diradical of 2 to 10 carbons or a substituted or unsubstituted 1,2-, 1,3- or 1,4-phenylene diradical,
the R22 substituents being alkyl radicals of 1 to 3 carbons, chloro or bromo; and Q is a recurring unit in an addition polymer of ethylenic monomers having a structure $$\underset{HO}{\overset{Ri}{\underset{O=C}{\diagdown}}}\overset{}{\underset{}{C}}-(CH_2)_t-\underset{\underset{G}{NH}}{\overset{Rii}{\underset{C=O}{|}}}$$

$$\underset{O=C-N-C=O}{\overset{Ri}{\diagdown}}\overset{}{\underset{}{C}}-(CH_2)_t-\underset{G}{\overset{Rii}{\underset{|}{C}-}} ,$$

in which the units occur in the polymer backbone or as pendant units or both, where Ri and Rii are the same or different and are hydrogen, an alkyl radical of 1 to 6 carbons, a cycloalkyl radical of 5 to 7 carbons, phenyl, chloro or bromo;

t is 0 or 1; and

G shows the point of attachment of group Q to the residue of Structure A1.

2. The process of claim 1, wherein

P is a peroxide-containing mono-radical having a structure:

$$R-OO-\underset{R3}{\overset{R2}{\underset{|}{C}}}-$$

or $$R-OO-\underset{OO---R}{\overset{R2}{\underset{|}{C}}}- ;$$

R is a substituted or unsubstituted t-alkyl radical of 4 to 12 carbons or a substituted or unsubstituted t-aralkyl radical of 9 to 13 carbons;

R11 is a substituted or unsubstituted alkylene diradical of 2 to 8 carbons;

$$X \text{ is} -\overset{O}{\underset{\|}{C}}-, \quad -O-\overset{O}{\underset{\|}{C}}- \quad \text{or} \quad -C(R2)(R3)-;$$

R22 is nothing or a substituted or unsubstituted alkylene diradical of 2 to 10 carbons; and Ri and Rii are the same or different and are hydrogen or an alkyl radical of 1 to 6 carbons.

3. The process of claim 2, wherein x is 1;

R is a substituted or unsubstituted t-alkyl radical of 4 to 12 carbons;

R22 is a substituted or unsubstituted alkylene diradical of 2 to 10 carbons;

Ri and Rii are hydrogen; and t is 0.

* * * * *